United States Patent
Brewer et al.

(10) Patent No.: US 7,155,277 B1
(45) Date of Patent: Dec. 26, 2006

(54) PATHWAY MANAGEMENT FOR CHF PATIENTS

(75) Inventors: James E. Brewer, Lino Lakes, MN (US); Mark W. Kroll, Simi Valley, CA (US); Scott H. Simcoe, Portland, OR (US)

(73) Assignee: Pacesetter, Inc., Sylmar, CA (US)

( * ) Notice: Subject to any disclaimer, the term of this patent is extended or adjusted under 35 U.S.C. 154(b) by 507 days.

(21) Appl. No.: 10/370,125

(22) Filed: Feb. 18, 2003

(51) Int. Cl.
*A61N 1/00* (2006.01)

(52) U.S. Cl. .......................................... 607/2

(58) Field of Classification Search ................ 128/903, 128/904, 920, 923; 607/2, 30–32, 59–60; 705/3
See application file for complete search history.

(56) References Cited

U.S. PATENT DOCUMENTS

| | | | |
|---|---|---|---|
| 6,270,457 B1 * | 8/2001 | Bardy | 600/300 |
| 6,277,072 B1 | 8/2001 | Bardy | 600/300 |
| 6,280,380 B1 | 8/2001 | Bardy | 600/300 |
| 6,336,903 B1 | 1/2002 | Bardy | 600/508 |
| 6,915,149 B1 * | 7/2005 | Ben-Haim | 600/374 |
| 2002/0143372 A1 * | 10/2002 | Snell et al. | 607/30 |

FOREIGN PATENT DOCUMENTS

WO    WO 01/43631 A1    6/2001

OTHER PUBLICATIONS

Shamsham M.D. et al., "Essentials of the Diagnosis of Heart Failure," Am. Fam. Phys., 61: 1319-1330 (Mar. 1, 2000).
Loh M.D., "Overview: Old and New Controversies in the Treatment of Advanced Congestive Heart Failure," J. Card. Fail. (2 Suppl. 1) 1-7 (2001).
Gomberg-Maitland M.D. et al., "Treatment of Congestive Heart Failure," Arch. Intern. Med., 161:342-349 (2001).

* cited by examiner

*Primary Examiner*—Robert Pezzuto
*Assistant Examiner*—Yun Haeng Lee

(57) ABSTRACT

An exemplary system and/or method allows for automated and/or semi-automated treatment of CHF, for example, via a pathway. Various exemplary systems and/or methods include a server and/or a client for creating, implementing and/or maintaining a CHF pathway. An exemplary client has a communication link with an implantable cardiac device for communicating one or more operational parameters to the implantable cardiac device and/or receiving information from the implantable cardiac device. Other exemplary systems and/or methods are also disclosed.

16 Claims, 29 Drawing Sheets

CLIENT SOFTWARE
870

PHYSICIAN/CLIENT
    Create, implement, and maintain optimal pathways/sub-pathways, etc.

MODIFY AN EXISTING PATHWAY
    Pathway/sub-pathways
    Optimizing models
      - historical data
      - demographic data
      - diagnostic data
      - therapeutic data
    Etc.

USER-INTERFACE - GENERAL
    Screens
    Charts
    Entry boxes
     - patient data
    Display
    Edit
    Etc.

USER-INTERFACE - ANALYTICAL
    Pathway graphs
    Statistics
    Cost of care
    Quality of life
    Length of life
    Etc.

COMMUNICATION
    Server
    DB
    Patient
     - device
     - input (e.g., Web-based, etc.)
    Etc.

Fig. 11

PATHWAY MANAGEMENT FOR CHF PATIENTS

TECHNICAL FIELD

The present invention generally relates to creation, implementation and/or maintenance of pathways, such as, therapeutic pathways for treatment of congestive heart failure.

BACKGROUND

Congestive heart failure (CHF) is a condition in which a weakened heart cannot pump enough blood to body organs. Heart failure may affect either the right side, left side, or both sides of the heart. As pumping action is lost, blood may back up into other areas of the body, including the liver, gastrointestinal tract, and extremities (right-sided heart failure), or the lungs (left-sided heart failure). Structural or functional causes of heart failure include high blood pressure (hypertension), valvular heart disease, congenital heart diseases, cardiomyopathy, heart tumor, and other heart diseases. Precipitating factors include infections with high fever or complicated infections, use of negative inotropic drugs (such as beta-blockers and calcium channel blocker), anemia, irregular heartbeats (arrhythmias), hyperthyroidism, and kidney disease.

CHF can perhaps be arrested, even temporarily remitted, but never cured due to the nature of its most common causes (coronary artery disease leading to myocardial infarction leading to permanently destroyed or damaged myocardial substrate). Therefore, a patient with CHF requires careful and attentive care and disease management, particularly as the disease state progresses. Regarding progressive states of CHF, the New York Heart Association (NYHA) has classified heart condition into four classes: Class I—patients with no limitation of activities; they suffer no symptoms from ordinary activities; Class II—patients with slight, mild limitation of activity; they are comfortable with rest or with mild exertion; Class III—patients with marked limitation of activity; they are comfortable only at rest; and Class IV—patients who should be at complete rest, confined to bed or chair; any physical activity brings on discomfort and symptoms occur at rest. Proper treatment of heart failure often relies on assessment of a patient's classification, see, e.g., Shamsham and Mitchell, "Essentials of the diagnosis of heart failure", *Am. Fam. Phys.*, Mar. 1, 2000 (pp. 1319–1330). For example, Shamsham and Mitchell present an algorithm for diastolic dysfunction and systolic dysfunction that references the NYHA classes.

While a variety of treatments exist for patients with decompensated CHF, see, e.g., Loh, "Overview: Old and new controversies in the treatment of advanced congestive heart failure", *J. Card. Fail.*, 7(2 Suppl. 1): 1–7 (2001); and Gomberg-Maitland, et al., "Treatment of congestive heart failure", *Arch. Intern. Med.*, 161: 342–349 (2001), a need exists for improved treatments, in addition, a need exists for merging treatment and diagnostics.

A physician's ability to treat a patient relies heavily on proper diagnosis of the patient's condition. Diagnosis typically involves categorizing and differentiating between many possible diseases and disease states. In the past, diagnosis usually depended on a physician's ability to use medical texts and personal knowledge together with consultation with other physicians, etc. With the onset of computers and digital databases, a plethora of information has become available to physicians and, in general, to a variety of healthcare workers. However, challenges still exist in managing such a large volume of information. Even greater challenges exist in integrating the information or using the information to create treatment pathways. As an example, a treatment pathway is a patient care algorithm, or path, that is intended to increase efficiency and thereby improve patient care. Thus, while computers have revolutionized storage and availability of information, a need exists for systems and/or methods to assist and/or manage in the diagnosis and/or treatment of disease, such as, but not limited to CHF.

Advances in computer technology have also led to improved implantable cardiac devices (ICDs), which are often indicated for at least some CHF patients. ICDs are implanted within the body of a patient to monitor, regulate, and/or correct heart function. ICDs include implantable cardiac stimulation devices (e.g., implantable cardiac pacemakers, implantable defibrillators) that apply stimulation therapy to the heart as well as implantable cardiac monitors that monitor heart activity.

ICDs typically include a control unit positioned within a casing that is implanted into the body and a set of leads that are positioned to impart stimulation and/or monitor cardiac activity. With improved processor and memory technologies, the control units have become increasingly more sophisticated, allowing them to monitor many types of conditions and apply tailored stimulation therapies in response to those conditions.

ICDs are typically capable of being programmed remotely by an external programming device, often called a "programmer". Today, individual ICDs are equipped with telemetry circuits that communicate with the programmer. One type of programmer utilizes an electromagnetic wand that is placed near the implanted cardiac device to communicate with the implanted device. The wand contains a coil that forms a transformer coupling with the ICD telemetry circuitry. The wand transmits low frequency signals by varying coil impedance.

Early telemetry systems were passive, meaning that the communication was unidirectional from the programmer to the implanted device. Passive telemetry allowed a treating physician to download instructions to the implanted device following implantation. Due to power and size constraints, early commercial versions of the implanted devices were incapable of transmitting information back to the programmer.

As power capabilities improved, active telemetry became feasible, allowing synchronous bi-directional communication between the implanted device and the programmer. Active telemetry utilizes a half-duplex communication mode in which the programmer sends instructions in a predefined frame format and, following termination of this transmission, the implanted device returns data using the frame format. With active telemetry, the treating physician is able to not only program the implanted device, but also retrieve information from the implanted device to evaluate heart activity and device performance. The treating physician may periodically want to review device performance or heart activity data for predefined periods of time to ensure that the device is providing therapy in desired manner. Consequently, current generation implantable cardiac therapy devices incorporate memories, and the processors periodically sample and record various performance parameter measurements in the memories.

Data pertaining to a patient's cardiac condition is gathered and stored by the programmer during programming sessions and/or follow-up monitoring of the ICDs. Analysis of the cardiac condition is performed locally by the programming software. Programmers offer comprehensive diagnostic capabilities, high-speed processing, and easy operation, thereby facilitating efficient programming and timely patient follow-up.

In addition to local analysis, TransTelephonic Monitoring (TTM) systems are employed to gather current cardiac data from patients who are remote from the healthcare provider. TTM systems are placed in patients' homes. They typically include a base unit that gathers information from the ICD much like the programmer would. The base unit is connected to a telephone network so that data may be transmitted to the medical staff responsible for that patient. An example of an ICD TTM system is a service from St. Jude Medical® and Raytel® Cardiac Services called "Housecall™." This service provides current programmed parameters and episode diagnostic information for a plurality of events including stored electrograms (EGMs). Real-time EGMs with annotated status information can also be transmitted.

Using a telephone and a transmitter, the TTM system provides both the medical staff and the patient the convenience of instant analysis of therapy without having the patient leave the comfort of home. Typically, real-time measurements are transmitted in just minutes. Patients may be closely monitored, and the medical staff has more control of their patient's treatment, thus administering better patient management.

Another challenge that still persists, however, is how to efficiently and effectively integrate patient information, device information and/or other sources of information to medical personnel and other knowledge workers who might have an interest in the device data. A yet larger challenge involves use such information in creating, implementing and/or maintaining treatment pathways, which optionally include use of an ICD. Indeed, a need exists for systems and/or methods that address these challenges.

SUMMARY

An exemplary system and/or method allows for automated and/or semi-automated treatment of CHF, for example, via a pathway. Various exemplary systems and/or methods include a server and/or a client for creating, implementing and/or maintaining a CHF pathway. An exemplary client has a communication link with an implantable cardiac device for communicating one or more operational parameters to the implantable cardiac device and/or receiving information from the implantable cardiac device. Other exemplary devices, systems and/or methods are also disclosed.

BRIEF DESCRIPTION OF THE DRAWINGS

FIG. 11 is a listing of exemplary client software functionalities.

DETAILED DESCRIPTION

Various parts of the following description set forth a cardiac therapy network architecture in which information from an implantable cardiac device is processed and/or distributed, for example, to a computer. It is anticipated that various knowledge workers will utilize any of a variety of different computing devices for receiving and viewing such information. These computing devices may vary widely in terms of their user interface (UI) capabilities.

Cardiac Therapy Network

Figure 1:
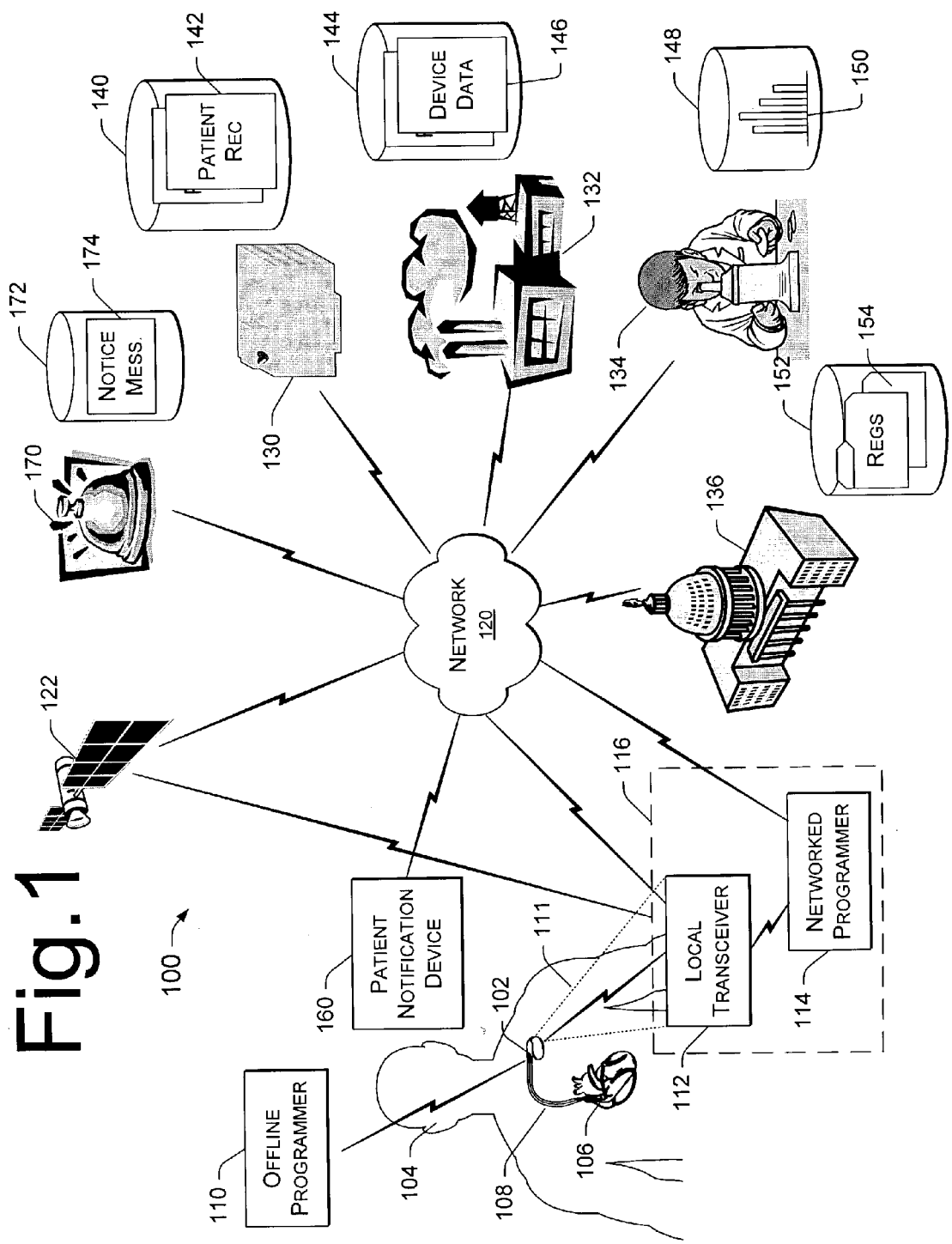
FIG. 1 is a diagrammatic illustration of a cardiac therapy network architecture with an implantable cardiac therapy device (ICD) connected to a network of computing systems used by various knowledge workers.

FIG. 1 shows an exemplary cardiac therapy network architecture 100 that includes an implantable cardiac device (ICD) 102 coupled to a network of that includes exemplary computing systems. The ICD is illustrated as being implanted in a human patient 104. The exemplary ICD 102 is in electrical communication with a patient's heart 106 by way of multiple leads 108 suitable for monitoring cardiac activity and/or delivering multi-chamber stimulation and shock therapy.

The ICD 102 optionally communicates with a standalone or offline programmer 110 via short-range telemetry technology. The offline programmer 110 is equipped with a wand that, when positioned proximal to the ICD 102, communicates with the ICD 102 through a magnetic coupling.

The ICD 102 can alternatively, or additionally, communicate with a local transceiver 112. The local transceiver 112 may be a device that resides on or near the patient, such as an electronic communications device that is worn by the patient or is situated on a structure within the room or residence of the patient. The local transceiver 112 communicates with the ICD 102 using short-range telemetry or longer-range high-frequency-based telemetry, such as RF (radio frequency) transmissions. Alternatively, the local transceiver 112 may be incorporated into the ICD 102, as represented by dashed line 111. In this case, the ICD includes a separate and isolated package area that accommodates high-frequency transmissions without disrupting operation of the monitoring and stimulation circuitry.

Depending upon the implementation and transmission range, the local transceiver 112 can be in communication with various other devices of the network architecture 100. One possible implementation is for the local transceiver 112 to transmit information received from the ICD 102 to a networked programmer 114, which is connected to network 120. The networked programmer 114 is similar in operation to standalone programmer 110, but differs in that it is connected to the network 120. The networked programmer 114 may be local to, or remote from, the local transceiver 112; or alternatively, the local transceiver 112 may be incorporated into the networked programmer 114, as represented by dashed line 116.

Another possible implementation is for the local transceiver to be connected directly to the network 120 for communication with remote computing devices and/or programmers. Still another possibility is for the local transceiver 112 to communicate with the network 120 via wireless communication, such as via a satellite system 122.

The network 120 may be implemented by one or more different types of networks (e.g., Internet, local area network, wide area network, telephone, cable, satellite, etc.), including wire-based technologies (e.g., telephone line, cable, fiber optics, etc.) and/or wireless technologies (e.g., RF, cellular, microwave, IR, wireless personal area network, etc.). The network 120 can be configured to support any number of different protocols, including HTTP (HyperText Transport Protocol), TCP/IP (Transmission Control Protocol/Internet Protocol), WAP (Wireless Application Protocol), Bluetooth, and so on.

A number of knowledge workers are optionally interested in information gathered from the implantable cardiac device 102. Representative knowledge workers include healthcare providers 130, the device manufacturer 132, clinical groups 134, and regulatory agencies 136. The knowledge workers are optionally interested in different portions of the information. For instance, the healthcare providers 130 typically have an interest in information pertaining to a particular patient's condition. The manufacturer 132 typically cares about how the device is operating. The clinical groups 134 may want certain information for inclusion in patient populations that can be studied and analyzed. The regulatory agencies 136 are generally concerned whether the devices, and various treatments administered by them, are safe or pose a health risk.

The network architecture 100 facilitates distribution of the device information to the various knowledge workers and/or computers. Information gathered from the device is optionally integrated, processed, and distributed to any of the various knowledge workers and/or computers. Computer systems maintain and store the device information, and optionally prepare the information for efficient presentation to the knowledge workers. The computer systems represented pictorially in FIG. 1 are generally shown as databases (e.g., a database-server arrangement, etc.). However, such a system can be implemented using a wide variety of computing devices, ranging from small handheld computers or portable digital assistants (PDAs) carried by physicians to workstations or mainframe computers with large storage capabilities. The healthcare providers 130 are equipped with computer systems 140 that store and process patient records 142. The manufacturer 132 has a computer system 144 that tracks device information 146 returned from ICDs 102. The clinical groups 134 generally have computer systems 148 that store and analyze information across patient populations, as represented by a histogram 150. The regulatory agencies 136 typically maintain computer systems 152 that register and track healthcare risk information 154 for ICDs.

The network architecture 100 supports two-way communication. Not only is information collected from the ICD 102 and distributed to the various computer systems of the knowledge workers, but also information can be returned from these computer systems to the networked programmer 114 and/or the local transceiver 112 for communication back to the ICD 102. Information returned to the ICD 102 may be used to adjust operation of the device, or modify therapies being applied by the device. Such information may be imparted to the ICD 102 automatically, without the patient's knowledge.

Additionally, information may be sent to a patient notification device 160 to notify the patient of some event or item. The patient notification device 160 can be implemented in a number of ways including, for example, as a telephone, a cellular phone, a pager, a PDA (personal digital assistant), a dedicated patient communication device, a computer, an alarm, and so on. Notifications may be as simple as an instruction to sound an alarm to inform the patient to call into the healthcare providers, or as complex as HTML-based pages with graphics and textual data to educate the patient. Notification messages sent to the patient notification device 160 can contain essentially any type of information related to cardiac medicinal purposes or device operation. Such information might include new studies released by clinical groups pertaining to device operation and patient activity (e.g., habits, diets, exercise, etc.), recall notices or operational data from the manufacturer, patient-specific instructions sent by the healthcare providers, or warnings published by regulatory groups.

Notifications can be sent directly from the knowledge worker to the patient. Additionally, the network architecture 100 may include a notification system 170 that operates computer systems 172 designed to create and deliver notification messages 174 on behalf of the knowledge workers. The notification system 170 delivers the messages in formats supported by the various types of patient notification devices 160. For instance, if the patient carries a pager, a notification message might consist of a simple text statement in a pager protocol. For a more sophisticated wireless-enabled PDA or Internet-oriented cellular phone, messages might contain more than text data and be formatted using WAP formats.

Figure 2:
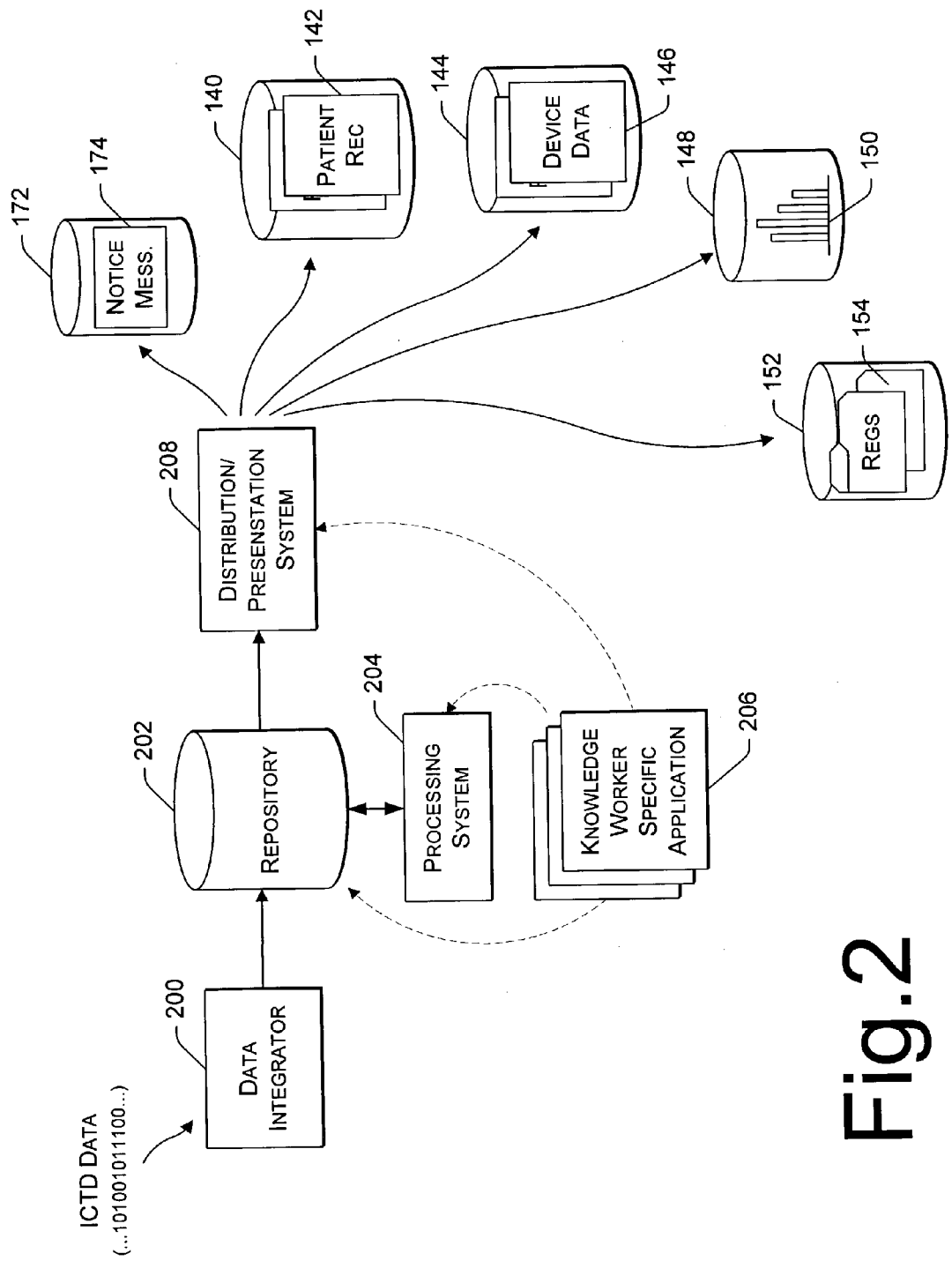
FIG. 2 is a functional diagram illustrating information flow from the ICD to the computing systems associated with the knowledge workers.

FIG. 2 shows an exemplary flow diagram of information (e.g., data) from the implantable cardiac device 102 to the various computer systems. Information from the ICD is typically output as digital data, as represented by the string of 0's and 1's. The data may consist of any number of items, including heart activity (e.g., IEGM), patient information, device operation, analysis results from on-device diagnostics, and so on.

A data integrator 200 accumulates the data and stores it in a repository 202. A processing system 204 processes portions of the data according to various applications 206 that are specifically tailored to place the data into condition for various knowledge workers and/or other devices. For example, healthcare workers might be interested in certain portions of the data, such as the IEGM data and the patient information. Clinical scientists might be interested in the heart data, but do not wish to see any patient information. Manufacturers may be interested in the raw data stream itself as a tool to discern how the device is operating. Depending on the needs of the end worker, the processing system 204 takes the raw device data, evaluates its accuracy and completeness, and generates different packages of data for delivery to the various knowledge workers. The processed data packages are also stored in the repository 202.

When the data is ready for delivery, a distribution/presentation system 208 distributes the different packages to the appropriate computer systems 140, 144, 148, 152, and 172. The distribution/presentation system 208 is configured to serve the packages according to the protocols and formats desired by the computer systems. In this manner, the network architecture 100 allows relevant portions of device data, collected from the ICD, to be disseminated to the appropriate knowledge workers in a form they prefer.

Once the ICD data is delivered, the computer systems 140, 144, 148, 152, and 172 store the data, present the data to the knowledge worker and/or communicate the data to one or more other devices. The computer systems may perform further processing specific to their use of the data. Through these processes, the knowledge workers and/or other devices create additional information that is useful to the patient, or other knowledge workers with interests in ICDs. For example, from the ICD data, the knowledge workers might devise improved therapies for a given patient, or create instructions to modify operation of a specific ICD, or gain a better understanding of how implantable cardiac devices operate in general, or develop better technologies for future generations of ICDs. Much of this created knowledge can be shared among the various knowledge workers and/or devices.

Figure 3:
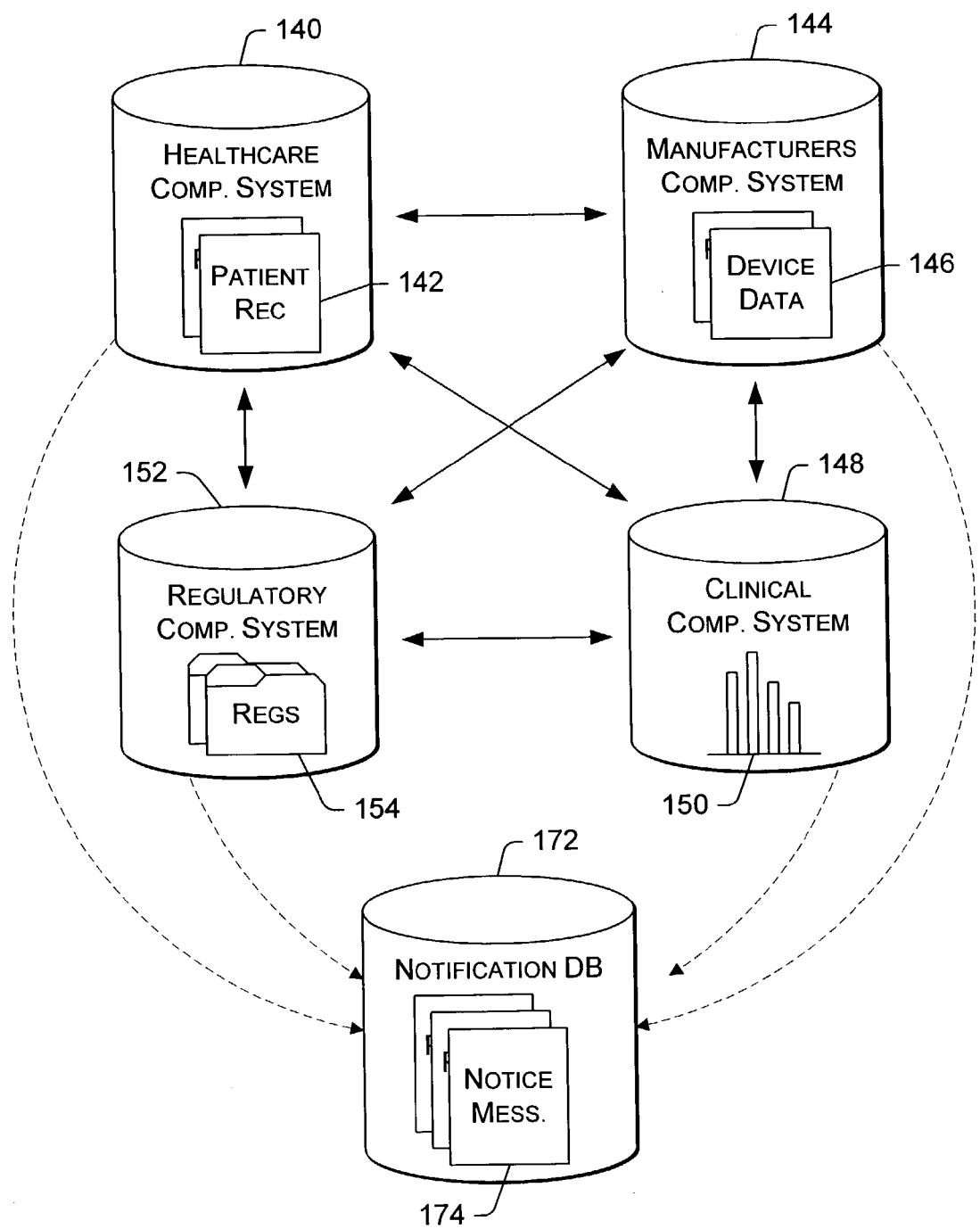
FIG. 3 is a functional diagram illustrating how the various computing systems share pieces of information to improve care given to the patient.

FIG. 3 shows how the various exemplary computing systems 140, 144, 148, 152, and 172 can cooperate and share pieces of information to improve the care given to a patient. Where appropriate and legally acceptable, the computer systems may be configured to pass non-private information among the various knowledge workers to better improve their understanding of the implantable medical field. Clinical results 150 produced by the clinical computer systems 148 may be shared with healthcare providers to improve patient care or with manufacturers to help in their design of next generation devices. The sharing of information may further lead to better and timelier healthcare for the patients.

If the collective knowledge base produces information that may prove helpful to the patient, that information can be passed to the notification system 172 for delivery to one or more patients. Also, any one of the knowledge workers may wish to employ the notification system 172 to send messages to the patient(s). Yet further, as described below, information optionally flows to an ICD to implement, maintain and/or modify a treatment pathway.

Figure 4:
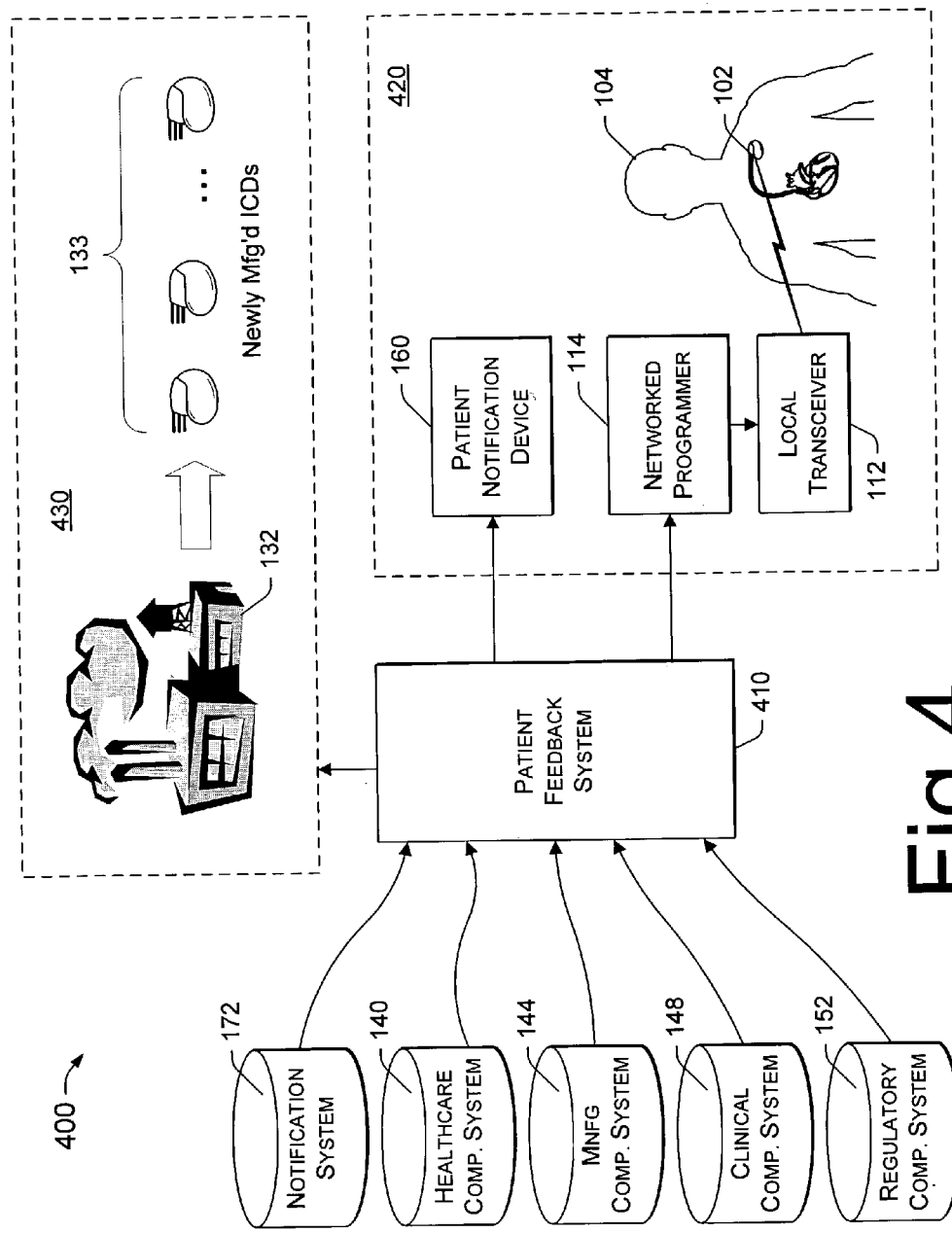
FIG. 4 is a functional diagram illustrating information flow from the computing systems back to the ICD.

FIG. 4 shows, in more detail, a flow scheme 400 wherein information flows to or from various computer systems (e.g., 140, 144, 148, 152, 172) used by the knowledge workers to the implantable cardiac device 102, the patient notification device 160 and or a manufacturing/programming operation 430. Information from any one of the computing systems—healthcare computer system(s) 140, manufacturer computer system(s) 144, clinical computer system(s) 148, regulatory computer system(s) 152—or the notification system 172 can be sent to a patient feedback system 410. The patient feedback system 410 facilitates delivery of the information back to the patient 104. It may be an independent system, or incorporated into one or more of the computing systems 140, 144, 148, 152, 172 and/or other system or device. For example, the patient feedback system 410 may be integrated into the notification system 172.

The patient feedback system 410 may be implemented in many ways. As one exemplary implementation, the patient feedback system 410 is implemented as a server that serves content back to the networked programmer 114, which then uses the information to program the ICD 102 through a built in transceiver 116, local transceiver 112, or wand-based telemetry. As another possible implementation, the patient feedback system may be a cellular or RF transmission system that sends information back to the patient notification device 160.

The network architecture 100 facilitates continuous care around the clock, regardless of where the patient is located. For instance, suppose the patient is driving in the car when a cardiac episode occurs. The ICD 102 detects the condition and transmits an alert message about the condition to the local transceiver 112. The message is processed and delivered to a physician's computer or PDA via the network 120. The physician can make a diagnosis and send some instructions back to the patient's ICD. The physician might also have a notification message that guides the patient to a nearest healthcare facility for further treatment sent via the notification system 172 to the patient's notification device 160. Concurrently, the physician can share the patient's records online with an attending physician at the healthcare facility so that the attending physician can review the records prior to the patient's arrival.

Exemplary ICD

Figure 5:
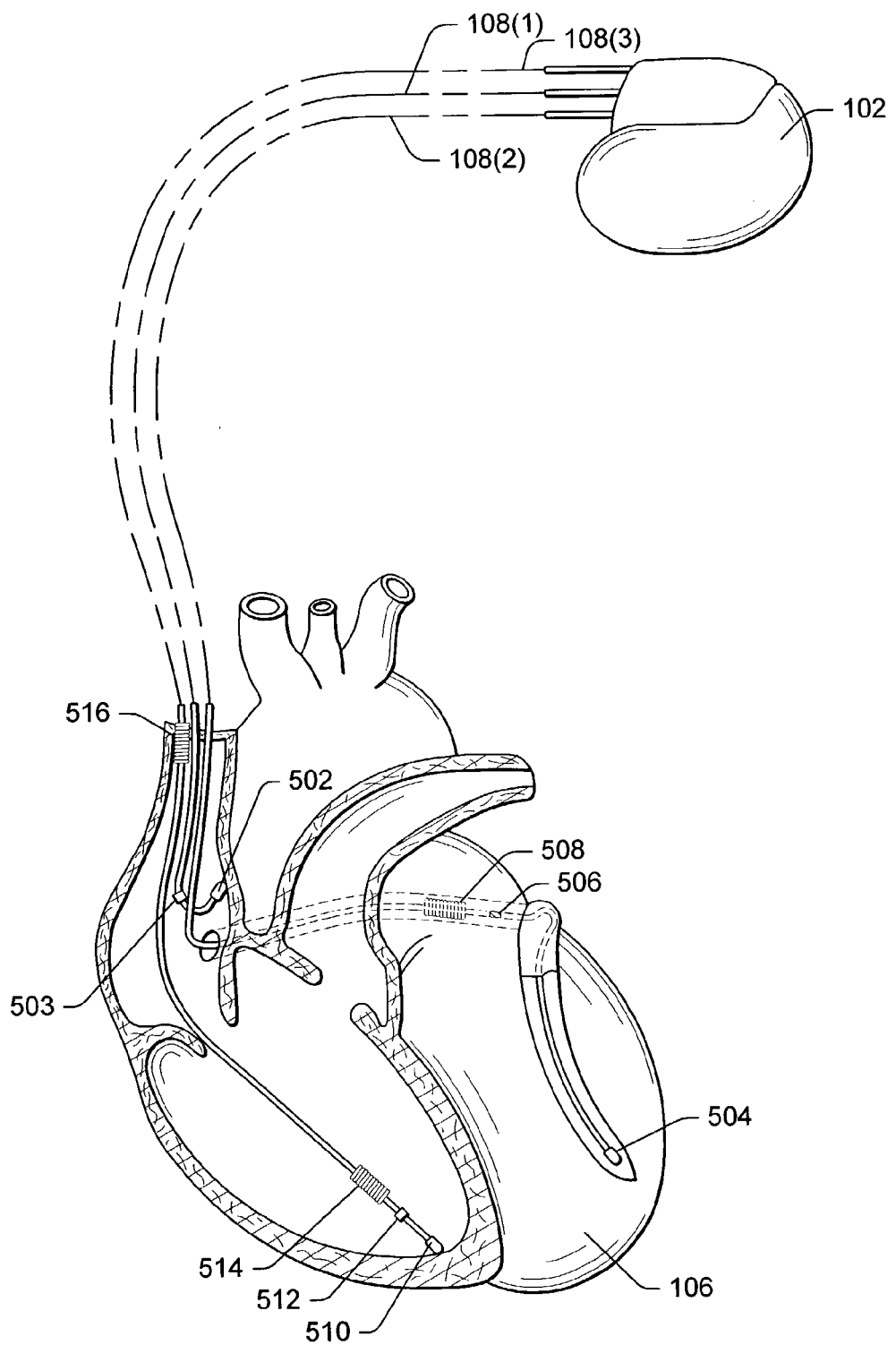
FIG. 5 is a simplified illustration of an ICD in electrical communication with a patient's heart for monitoring heart activity and/or delivering stimulation therapy.

FIG. 5 shows an exemplary ICD 102 in electrical communication with a patient's heart 106 for monitoring heart activity and/or delivering stimulation therapy, such as pacing or defibrillation therapies. The ICD 102 is in electrical communication with a patient's heart 106 by way of three leads 108(1)—(3). To sense atrial cardiac signals and to provide right atrial chamber stimulation therapy, the ICD 102 is coupled to an implantable right atrial lead 108(1) having at least an atrial tip electrode 502, which typically is implanted in the patient's right atrial appendage or septum. As shown in FIG. 5, the lead 108(1) also includes an atrial ring electrode 503 suitable for sensing and/or pacing. To sense left atrial and ventricular cardiac signals and to provide left chamber pacing therapy, the ICD 102 is coupled to a coronary sinus lead 108(2) designed for placement in the coronary sinus region via the coronary sinus. The coronary sinus lead 108(2) positions a distal electrode adjacent to the left ventricle and/or additional electrode(s) adjacent to the left atrium. An exemplary coronary sinus lead 108(2) is designed to receive atrial and ventricular cardiac signals and to deliver left ventricular pacing therapy using at least a left ventricular tip electrode 504, left atrial pacing therapy using at least a left atrial ring electrode 506, and shocking therapy using at least a left atrial coil electrode 508.

The ICD 102 is also shown in electrical communication with the patient's heart 106 by way of an implantable right ventricular lead 108(3) having, in this implementation, a right ventricular tip electrode 510, a right ventricular ring electrode 512, a right ventricular (RV) coil electrode 514, and a superior vena cava (SVC) coil electrode 516. Typically, the right ventricular lead 108(3) is transvenously inserted into the heart 102 to place the right ventricular tip electrode 510 in the right ventricular apex so that the RV coil electrode 514 will be positioned in the right ventricle and the SVC coil electrode 516 will be positioned in the superior vena cava. Accordingly, the right ventricular lead 108(3) is capable of receiving cardiac signals, and delivering stimulation in the form of pacing and shock therapy to the right ventricle.

Figure 6:
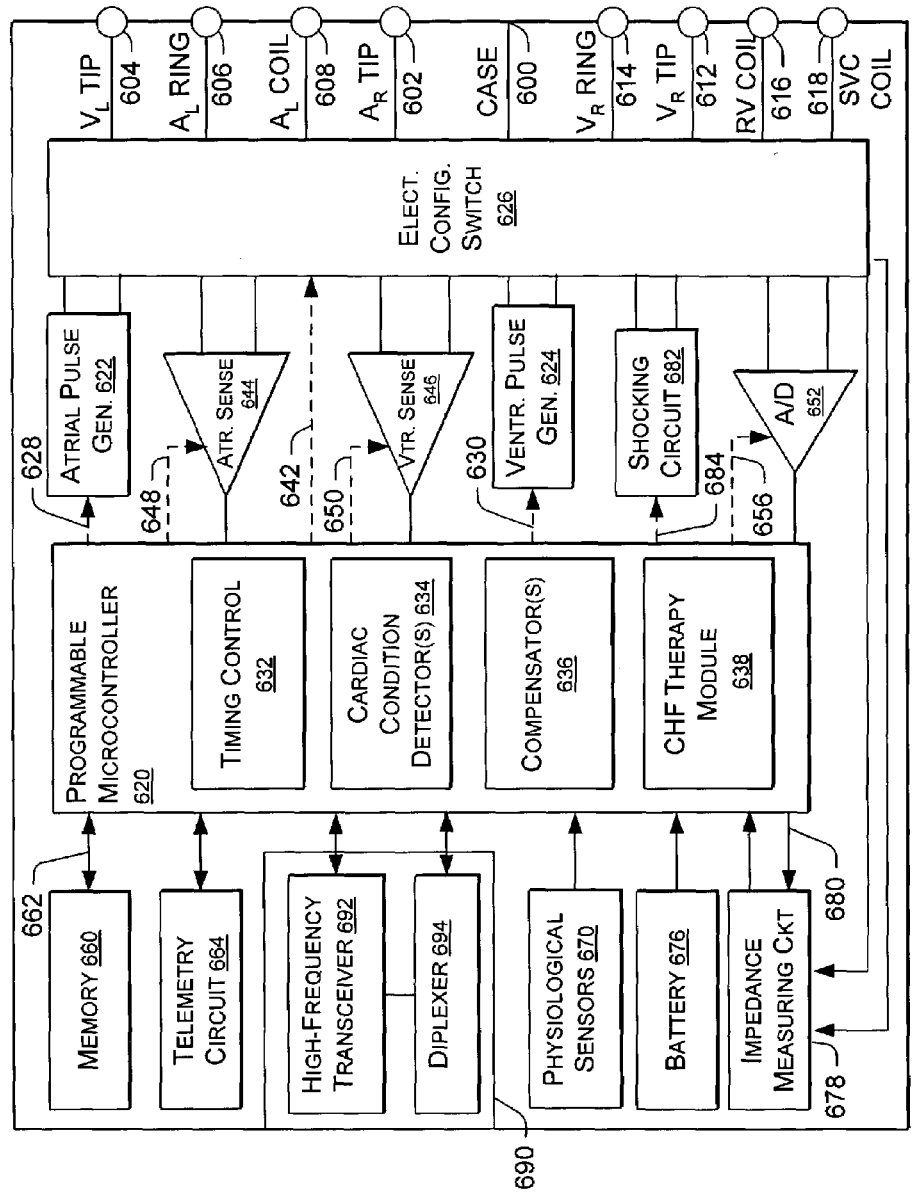
FIG. 6 is a functional block diagram of an exemplary implantable cardiac therapy device.

FIG. 6 shows an exemplary, simplified block diagram depicting various components of the ICD 102. The ICD 102 can be configured to perform one or more of a variety of functions including, for example, monitoring heart activity, monitoring patient activity, and treating fast and slow arrhythmias with stimulation therapy that includes cardioversion, defibrillation, and pacing stimulation. While a particular multi-chamber device is shown, it is to be appreciated and understood that this is done for illustration purposes.

The circuitry is housed in housing 600, which is often referred to as the "can", "case", "encasing", or "case electrode", and may be programmably selected to act as the return electrode for unipolar modes. Housing 600 may further be used as a return electrode alone or in combination with one or more of the coil electrodes for shocking purposes. Housing 600 further includes a connector (not shown) having a plurality of terminals 602, 604, 606, 608, 612, 614, 616, and 618 (shown schematically and, for convenience, the names of the electrodes to which they are connected are shown next to the terminals).

To achieve right atrial sensing and pacing, the connector includes at least a right atrial tip terminal ($A_R$ TIP) 602 adapted for connection to the atrial tip electrode 502. To achieve left chamber sensing, pacing, and shocking, the connector includes at least a left ventricular tip terminal ($V_L$ TIP) 604, a left atrial ring terminal ($A_L$ RING) 606, and a left atrial shocking terminal ($A_L$ COIL) 608, which are adapted for connection to the left ventricular ring electrode 504, the left atrial ring electrode 506, and the left atrial coil electrode 508, respectively. To support right chamber sensing, pacing, and shocking, the connector includes a right ventricular tip terminal ($V_R$ TIP) 612, a right ventricular ring terminal ($V_R$ RING) 614, a right ventricular shocking terminal (RV COIL) 616, and an SVC shocking terminal (SVC COIL) 618, which are adapted for connection to the right ventricular tip electrode 510, right ventricular ring electrode 512, the RV coil electrode 514, and the SVC coil electrode 516, respectively. Of course, other terminals are possible, for example, an atrial ring electrode for the atrial ring electrode 503.

At the core of the ICD 102 is a programmable microcontroller 620 that controls various operations of the ICD, including cardiac monitoring and stimulation therapy. Microcontroller 620 includes a microprocessor (or equivalent control circuitry), RAM and/or ROM memory, logic and timing circuitry, state machine circuitry, and I/O circuitry. Microcontroller 620 includes the ability to process or monitor input signals (data) as controlled by a program code stored in a designated block of memory. Any suitable microcontroller 620 may be used. The use of microprocessor-based control circuits for performing timing and data analysis functions are well known in the art.

For discussion purposes, microcontroller 620 is illustrated as including timing control circuitry 632 to control the timing of the stimulation pulses (e.g., pacing rate, atrioventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, and so on. Microcontroller 220 may further include various types of cardiac condition detectors 634 (e.g., an arrhythmia detector, a morphology detector, etc.) and various types of compensators 636 (e.g., orthostatic compensator, syncope response module, etc.). The microcontroller 220 further includes a CHF therapy module 238, which may help select and/or administer CHF therapy. This particular module optionally functions according to various exemplary methods described herein. These components can be utilized by the device 102 for determining desirable times to administer various therapies. The components 632–638 may be implemented in hardware as part of the microcontroller 620, or as software/firmware instructions programmed into the device and executed on the microcontroller 620 during certain modes of operation.

The ICD 102 further includes an atrial pulse generator 622 and a ventricular pulse generator 624 that generate pacing stimulation pulses for delivery by the right atrial lead 108(1), the coronary sinus lead 108(2), and/or the right ventricular lead 108(3) via an electrode configuration switch 626. It is understood that in order to provide stimulation therapy in each of the four chambers of the heart, the atrial and ventricular pulse generators, 622 and 624, may include dedicated, independent pulse generators, multiplexed pulse generators, or shared pulse generators. The pulse generators 622 and 624 are controlled by the microcontroller 620 via appropriate control signals 628 and 630, respectively, to trigger or inhibit the stimulation pulses.

The electronic configuration switch 626 includes a plurality of switches for connecting the desired electrodes to the appropriate I/O circuits, thereby providing complete electrode programmability. Accordingly, switch 626, in response to a control signal 642 from the microcontroller 620, determines the polarity of the stimulation pulses (e.g., unipolar, bipolar, combipolar, etc.) by selectively closing the appropriate combination of switches (not shown).

Atrial sensing circuits 644 and ventricular sensing circuits 646 may also be selectively coupled to the right atrial lead 108(1), coronary sinus lead 108(2), and the right ventricular lead 108(3), through the switch 626 to detect the presence of cardiac activity in each of the four chambers of the heart. Accordingly, the atrial (ATR. SENSE) and ventricular (VTR. SENSE) sensing circuits, 644 and 646, may include dedicated sense amplifiers, multiplexed amplifiers, or shared amplifiers. Each sensing circuit 644 and 646 may further employ one or more low power, precision amplifiers with programmable gain and/or automatic gain control, bandpass filtering, and a threshold detection circuit to selectively sense the cardiac signal of interest. The automatic gain control enables the ICD 102 to deal effectively with the difficult problem of sensing the low amplitude signal characteristics of atrial or ventricular fibrillation. Switch 626 determines the "sensing polarity" of the cardiac signal by selectively closing the appropriate switches. In this way, the clinician may program the sensing polarity independent of the stimulation polarity.

The outputs of the atrial and ventricular sensing circuits 644 and 646 are connected to the microcontroller 620 which, in turn, is able to trigger or inhibit the atrial and ventricular pulse generators 622 and 624, respectively, in a demand fashion in response to the absence or presence of cardiac activity in the appropriate chambers of the heart. The sensing circuits 644 and 646 receive control signals over signal lines 648 and 650 from the microcontroller 620 for purposes of controlling the gain, threshold, polarization charge removal circuitry (not shown), and the timing of any blocking circuitry (not shown) coupled to the inputs of the sensing circuits 644 and 646.

Cardiac signals are also applied to inputs of an analog-to-digital (A/D) data acquisition system 652. The data acquisition system 652 is configured to acquire intracardiac electrogram signals, convert the raw analog data into a digital signal, and store the digital signals for later processing and/or telemetric transmission to an external device 654. The data acquisition system 652 is coupled to the right atrial lead 108(1), the coronary sinus lead 108(2), and the right ventricular lead 108(3) through the switch 626 to sample cardiac signals across any pair of desired electrodes.

The data acquisition system 652 may be coupled to the microcontroller 620, or other detection circuitry, to detect an evoked response from the heart 106 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 620 detects a depolarization signal during a window following a stimulation pulse, the presence of which indicates that capture has occurred. The microcontroller 620 enables capture detection by triggering the ventricular pulse generator 624 to generate a stimulation pulse, starting a capture detection window using the timing control circuitry 632 within the microcontroller 620, and enabling the data acquisition system 652 via control signal 656 to sample the cardiac signal that falls in the capture detection window and, based on the amplitude, determines if capture has occurred.

The microcontroller 620 is further coupled to a memory 660 by a suitable data/address bus 662, wherein the programmable operating or operational parameters used by the microcontroller 620 are stored and modified, as required, in order to customize the operation of the implantable device 102 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 106 within each respective tier of therapy. With memory 660, the ICD 102 is able to sense and store a relatively large amount of data (e.g., from the data acquisition system 652), which may transmitted to the external network of knowledge workers for subsequent analysis.

Operating parameters of the ICD 102 may be non-invasively programmed into the memory 660 through a telemetry circuit 664 in telemetric communication with an external device, such as a programmer 110 or local transceiver 112. The telemetry circuit 664 advantageously allows intracardiac electrograms and status information relating to the operation of the device 102 (as contained in the microcontroller 620 or memory 660) to be sent to the external devices.

The ICD 102 can further include one or more physiologic sensors 670, commonly referred to as "rate-responsive" sensors because they are typically used to adjust pacing stimulation rate according to the exercise state of the patient. However, the physiological sensor 670 may further be used to detect changes in cardiac output, changes in the physiological condition of the heart, or diurnal changes in activity (e.g., detecting sleep and wake states, detecting position or postural changes, etc.). Accordingly, the microcontroller 620 responds by adjusting the various pacing parameters (such as rate, AV Delay, V—V Delay, etc.) at which the atrial and ventricular pulse generators, 622 and 624, generate stimulation pulses. While shown as being included within the device 102, it is to be understood that the physiologic sensor 670 may also be external to the device 102, yet still be implanted within or carried by the patient. Examples of physiologic sensors that may be implemented in device 102 include known sensors that, for example, sense respiration rate and/or minute ventilation, pH of blood, ventricular gradient, and so forth.

The ICD 102 additionally includes a battery 676 that provides operating power to all of circuits shown in FIG. 6. If the device 102 is configured to deliver pacing or shocking therapy, the battery 676 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 676 also desirably has a predictable discharge characteristic so that elective replacement time can be detected. As one example, the device 102 employs lithium/silver vanadium oxide batteries.

The ICD 102 can further include magnet detection circuitry (not shown), coupled to the microcontroller 620, to detect when a magnet is placed over the device 102. A magnet may be used by a clinician to perform various test functions of the device 102 and/or to signal the microcontroller 620 that the external programmer is in place to receive or transmit data to the microcontroller 620 through the telemetry circuits-664.

The ICD 102 further includes an impedance measuring circuit 678 that is enabled by the microcontroller 620 via a control signal 680. Uses for an impedance measuring circuit 678 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 678 is advantageously coupled to the switch 626 so that any desired electrode may be used.

In the case where the device 102 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 620 further controls a shocking circuit 682 by way of a control signal 684. The shocking circuit 682 generates shocking pulses of low (e.g., up to 0.5 joules), moderate (e.g., 0.5–10 joules), or high energy (e.g., 11 to 40 joules), as controlled by the microcontroller 620. Such shocking pulses are applied to the patient's heart 106 through at least two shocking electrodes, and as shown in this implementation, selected from the left atrial coil electrode 508, the RV coil electrode 514, and/or the SVC coil electrode 516. As noted above, the housing 600 may act as an active electrode in combination with the RV coil electrode 514, or as part of a split electrical vector using the SVC coil electrode 516 or the left atrial coil electrode 508 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5–40 joules), delivered asynchronously (since R-waves may be too disorganized), and pertaining exclusively to the treatment of fibrillation. Accordingly, the microcontroller 620 is capable of controlling the synchronous or asynchronous delivery of the shocking pulses.

The ICD 102 may further be designed with the ability to support high-frequency wireless communication, typically in the radio frequency (RF) range. As illustrated in FIG. 6, the can 600 may be configured with a secondary, isolated casing 690 that contains circuitry for handling high-frequency signals. Within this separate case 690 are a high-frequency transceiver 692 and a diplexer 694. High-frequency signals received by a dedicated antenna, or via leads 108, are passed to the transceiver 692. Due to the separate casing region 690, the transceiver handles the high-frequency signals in isolation apart from the cardiac therapy circuitry. In this manner, the high-frequency signals can be safely handled, thereby improving telemetry communication, without adversely disrupting operation of the other device circuitry.

Exemplary Computing Device

Figure 7:
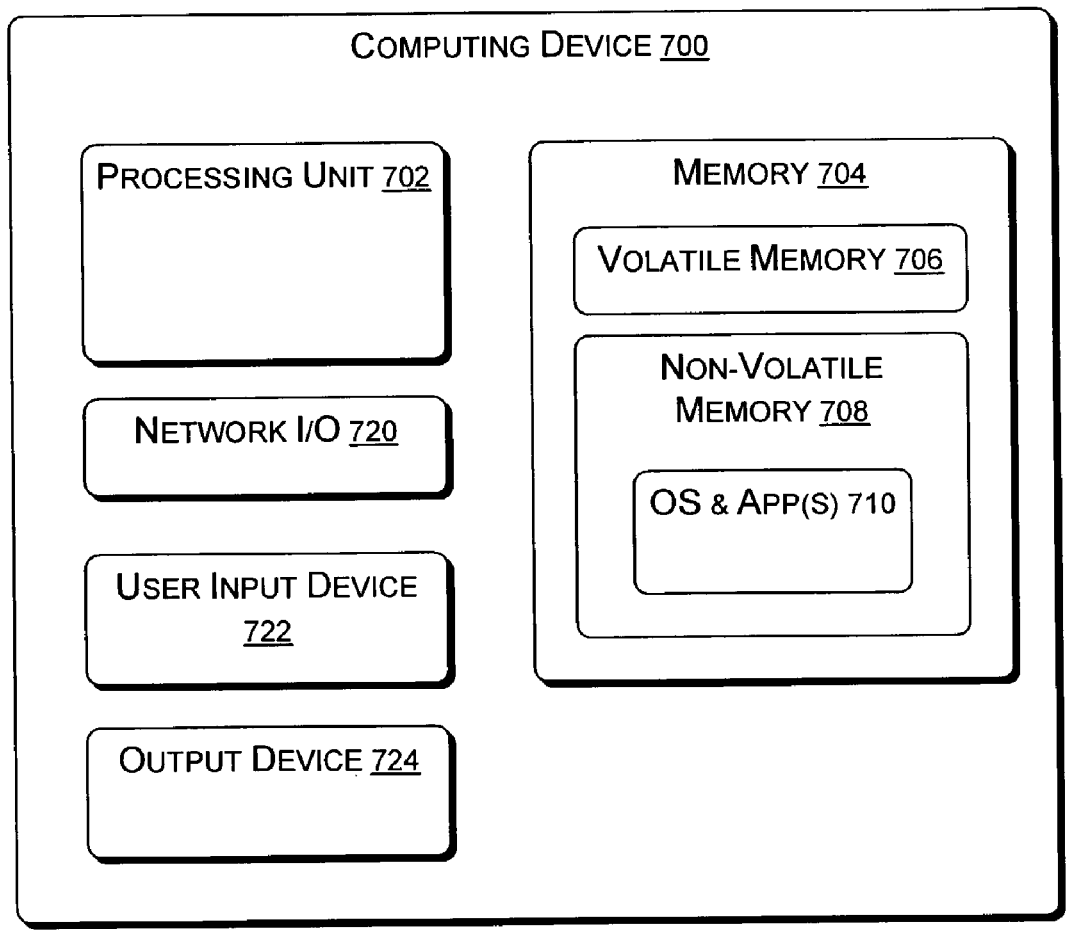
FIG. 7 is a functional block diagram of an exemplary computing device that may be used in the computing systems of the cardiac therapy network architecture.

FIG. 7 shows an exemplary computing device 700 employed in the computing systems of the cardiac therapy network architecture 100 and optionally employed in other exemplary systems and/or methods disclosed herein. It includes a processing unit 702 and memory 704. Memory 704 includes both volatile memory 706 (e.g., RAM) and non-volatile memory 708 (e.g., ROM, EEPROM, Flash, disk, optical discs, persistent storage, etc.). An operating system (OS) and various application programs (APP(S)) 710 are stored in non-volatile memory 708. When a program is running, various instructions are loaded into volatile memory 706 and executed by processing unit 702. Examples of possible applications that may be stored and executed on the computing device include the knowledge worker specific applications 206 shown in FIG. 2.

The computing device 700 may further be equipped with a network I/O connection 720 to facilitate communication with a network. The network I/O 720 may be a wire-based connection (e.g., network card, modem, etc.) or a wireless connection (e.g., RF transceiver, Bluetooth device, etc.). The computing device 700 may also include a user input device 722 (e.g., keyboard, mouse, stylus, touch pad, touch screen, voice recognition system, etc.) and an output device 724 (e.g., monitor, LCD, speaker, printer, etc.).

Various aspects of the methods and systems described throughout this disclosure may be implemented in computer software or firmware as computer-executable instructions. When executed, these instructions direct the computing device (alone, or in concert with other computing devices of the system) to perform various functions and tasks that enable the cardiac therapy network architecture 100.

Exemplary Systems and Methods

Figure 8:
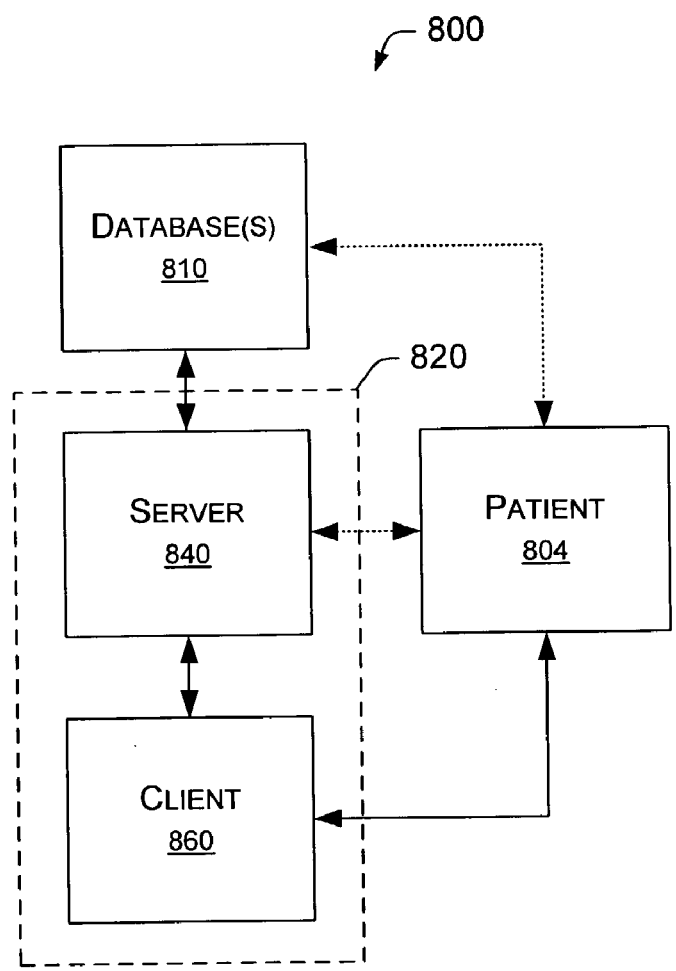
FIG. 8 is a functional block diagram of an exemplary system and/or method for managing one or more patient pathways.

FIG. 8 shows an exemplary system and/or method 800 for managing a clinical pathway of a CHF patient. A database block 810 includes one or more databases that contain information germane to a clinical pathway and/or a CHF patient, for example, the CHF patient 804. Of course, the one or more databases of the database block 810 optionally include associated servers. The exemplary system and/or method 800 also includes a client-server block 820, which includes a server block 840 and a client block 860 wherein the client block 860 and the server block 840 have a communication link suitable for typical client-server operations. According to this exemplary system and/or method 800, the client-server block 820 has a communication link with the database block 810. For example, as shown, the database block 810 has a communication link with the server block 840. Of course, the database block 810 may also have a communication link with the client block 860. In addition, the patient 804 has a communication link with the client block 860 and optionally the server block 840 and/or the database block 810. The exemplary system and/or method 800 optionally include various components of the cardiac therapy network architecture 100 of FIG. 1. For example, various aforementioned communication links of the exemplary system and/or method 800 include network communication links.

Figure 9:
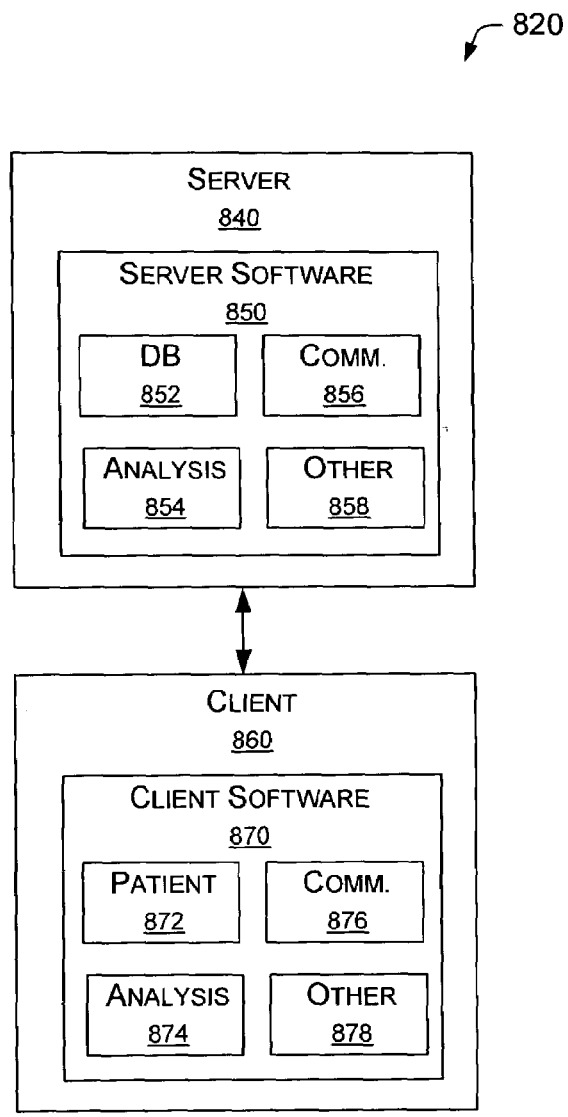
FIG. 9 is a function block diagram of an exemplary client-server system and/or method.

FIG. 9 shows the exemplary client-server block 820 of FIG. 8 in more detail. In particular, the server block 840 includes a server software block 850 and the client block 860 includes a client software block 870. The server software block 850 includes a database software block 852, an analysis software block 854, a communication software block 856, and a block 858 that includes other software; while, the client software block 870 includes a patient software block 872, an analysis software block 874, a communication software block 876, and a block 878 that includes other software. In general, the client-server block 820 (e.g., through use of such software blocks, etc.) is capable of managing pathways for one or more CHF patients.

Figure 10:
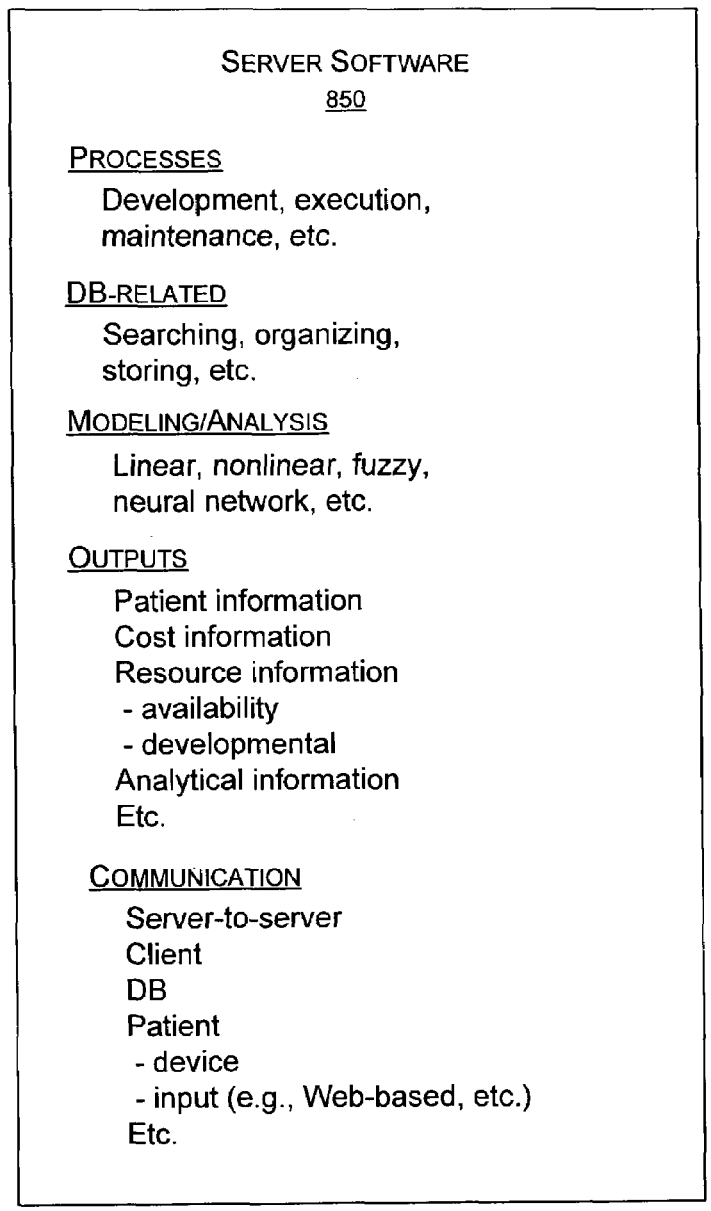
FIG. 10 is a listing of exemplary server software functionalities.

FIG. 10 shows the server software block 850 of FIG. 9 along with various exemplary functions. For example, the server software block 850 generally includes software capable of performing operations related to development, execution, and maintenance of clinical information. More specifically, the database block 852 optionally includes software for searching information, organizing information, storing information, etc.; the analysis block 854 optionally includes software for modeling, such as, but not limited to, statistical, linear, nonlinear, fuzzy logic, and/or neural network modeling; the other block 858 optionally includes software for outputting information, such as, but not limited to, patient, cost, resource, and/or analytical information; and the communication block 858 optionally includes software for server—server, server-client, database, patient (e.g., device, patient, physician-patient, etc.) and/or other communication tasks.

FIG. 11 shows the client software block 870 of FIG. 9 along with various exemplary functions. For example, the client software block 870 generally includes software capable of performing operations related to creation, implementation, and maintenance of pathways, such as, optimal pathways and/or associated sub-pathways. For example, the patient block 872 includes software for creation, implementation and/or maintenance of optimal pathways for one or more patient. The analysis block 874 typically includes software to aid in pathway creation, implementation and/or maintenance. For example, the analysis block 874 optionally includes software to modify an existing pathway and/or to create a pathway based on a pathway model provided another computer system (e.g., the server 840). Such exemplary analytical software is typically suitable to create and/or modify a pathway (e.g., pathway, optimal pathway, sub-pathway, etc.). Creation and/or modification optionally involve analysis based, at least in part, on historical data, demographic data, diagnostic data, etc. Such data may pertain to a specific patient and/or group of patients (e.g., patients having implanted cardiac device, patients having certain symptoms, patients having certain similarities, etc.).

The client software 870 typically further includes user-interface software, for example, in the other software block 878 of the exemplary client 860 of FIG. 9. User-interface software optionally includes general and analytical user-interfaces. General user-interface software typically includes software for screens, charts, entries (e.g., patient data, cost data, resource data, etc.), displays, editing, etc. Analytical user-interface software typically includes software for user-interaction with analyses, such as, but not limited to, statistical analyses and/or analytical models germane to cost of care information, quality of life information, length of life information, resource information, and, in general, pathway creation, implementation and/or maintenance. For example, analytical user-interface software optionally allows a user (e.g., physician, etc.) to enter desirable and/or target information with respect to time. Consider graphical entry of target cost of care information wherein a user sketches a graph (or points) for an approximate 10 year period; on the basis of such an entry, analysis software may create an optimal pathway that accounts for optimal quality of life given the cost of care information. Of course, an exemplary client 860 optionally pulls such cost of care information and/or other information from a database and/or other resource (e.g., network resource, etc.).

The exemplary client software 870 of FIG. 11 also includes communication software (see, e.g., the communication software block 878 of FIG. 9). The communication software typically includes software for client-server communication, database communication, patient-client communication, etc. Patient-client communication optionally occurs via a patient associated medical device (e.g., implanted device, sensor device, etc.) in communication with the client and/or via direct and/or indirect patient input via a communication device (e.g., networked computer, telephone, pager, etc.) in communication with the client. Consider a Web-based application that displays a Web-page on a networked patient computer wherein the patient enters information according to queries presented on the Web-page. Of course, such information may optionally reach a client (e.g., the client 860) indirectly, for example, via a server (e.g., the server 840).

Figure 12:
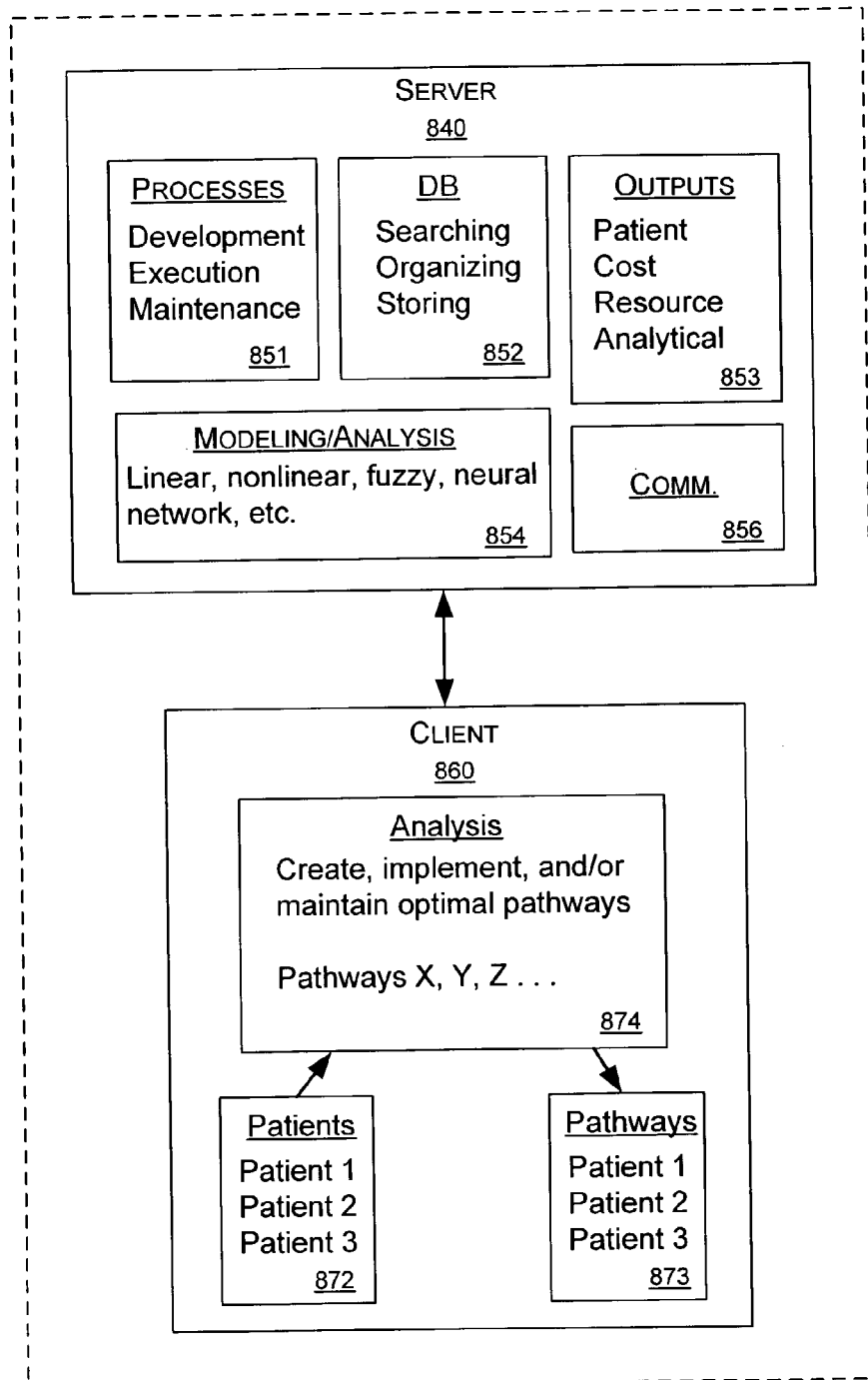
FIG. 12 is a functional block diagram of an exemplary client-server system and/or method.

FIG. 12 shows the exemplary client-server system and/or method 820 (see, e.g., description of FIGS. 8–11) for pathway management of a patient (e.g., a CHF patient). The server 840 includes various functional blocks, including a processes block 851, a database block 852, an outputs block 853, a modeling/analysis block 854, and a communication block 856. The processes block 851 includes functionality for development, execution and/or maintenance of resources suitable for aiding pathway management. The database block 852 includes functionality for searching, organizing, and/or storing information. The outputs block 853 includes functionality for outputting patient, cost, resource, and/or analytical information. The modeling/analysis block 854 includes functionality for making available one or more analytical models to the client 860 and/or other client, etc. The communication block 856 includes functionality for communicating information.

The client 874 includes various functional blocks as well, including a patient block 872, an analysis block 874 and a pathways block 873. The patient block 872 includes functionality for inputting and/or selecting patient information (e.g., Patient 1, Patient 2, Patient 3, etc.). The analysis block 874 includes functionality for creating, implementing and/or maintaining one or more optimal pathways (e.g., Pathway X, Pathway Y, Pathway Z, etc.). The pathways block 873 includes functionality for linking one or more pathways (e.g., Pathway X, Pathway Y, Pathway Z, etc.) with one or more patients (e.g., Patient 1, Patient 2, Patient 3, etc.). According to such an exemplary system and/or method, a user inputs and/or selects a patient (e.g., the patient block 872). Of course, a client may optionally perform such input and/or selection automatically (e.g., user programmed input and/or selection, etc.). Next, the client 860 creates one or more suitable pathways for the patient (e.g., the analysis block 874) wherein the pathways optionally stem from and/or depend on pathway models made available by the server 840. Of course, the client 860 may create only one pathway for the patient, for example, an optimal pathway; however, during this process, several potentially suitable pathways are optionally created which may emphasize a certain criterion or criteria (e.g., cost of care, quality of life information, length of life, etc.). Further, various sub-pathways are optionally created during this process. This process optionally occurs automatically without a user; however, user interaction is also possible in the creation and/or selection of one or more pathways. Finally, the client 860 outputs and/or implements one or more pathways accordingly for the patient. This process optionally occurs automatically without a user; however, user interaction is also possible in the output and/or implementation.

Figure 13:
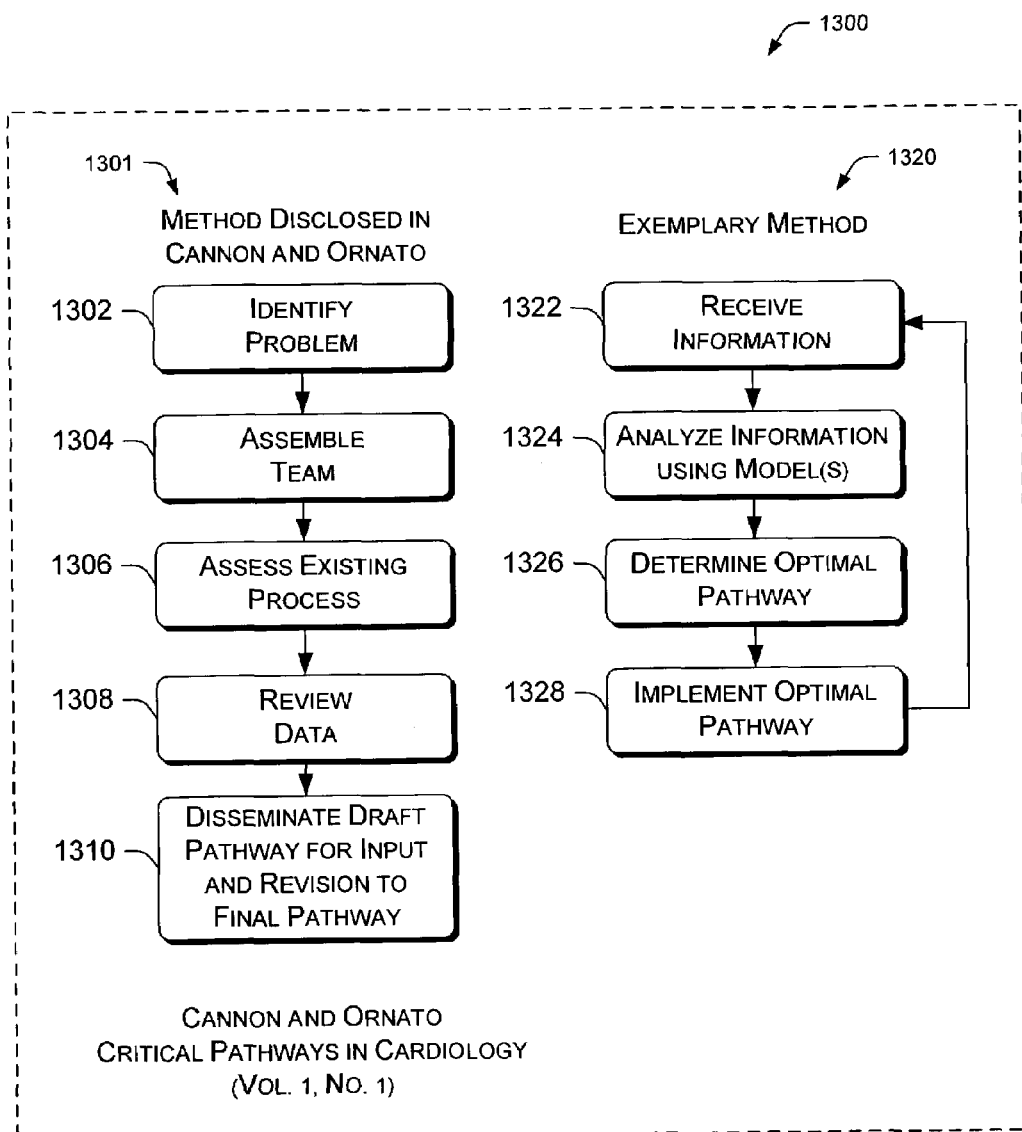
FIG. 13 is a functional block diagram of two methods for pathways.

FIG. 13 shows two pathway methods 1300. One pathway method 1301, from the reference Cannon and Ornato, "How to develop a critical pathway", *Critical Pathways in Cardiology*, Vol. 1, No. 1, pp. 53–60 (2002) illustrates steps in "critical pathway development". The other pathway method 1320 illustrates an exemplary method according to various aspects disclosed herein.

The pathway method 1301 includes an identification block 1302 wherein development of a pathway begins with identifying a problem, "such as underuse of newly available effective therapies (clopidogrel, glycoprotein IIb/IIIa inhibitors, and low molecular weight heparin) and underutilization of existing therapies (aspirin, heparin, and beta-blockers) for ACS [acute coronary syndromes]", Cannon and Ornato, p. 55. An assemblage block 1304 follows wherein a multidisciplinary team should be assembled that includes representatives from all groups that would be affected by the pathways and whose buy-in would be needed for implementation", Cannon and Ornato, p. 55. Next, an assessment block 1306 "involves an assessment of current emergency department and cardiology practices for ACS", Cannon and Ornato, p. 55. A review data block 1308 includes team or committee review of "the literature to identify the best practices and optimal processes of care", Cannon and Ornato, p. 55. Following review, dissemination of a draft pathway for input and revision to a final pathway occurs in a dissemination and revision block 1310. According to the dissemination and revision block 1310, a critical pathway includes "a time mask matrix in which specific tasks are organized along a timeline" and further, according to Cannon and Ornato, p. 56, "if the pathway format is too difficult to follow, it will not be used". In the pathway method 1301 disclosed in Cannon and Ornato, only after revision of a final pathway does implementation occur. Implementation typically involves issuance of "standard orders" which may include tools such as wall charts, pocket cards, simple checklists and thrombolysis in myocardial infarction (TIMI) risk calculators.

Regarding TIMI risk calculators, Cannon and Ornato discuss a Palm handheld device capable of calculating a TIMI risk score for a patient and, in response thereof, providing outcomes for a patient from several large trials and showing the benefits of new therapies. This device may also provide a ST elevation MI risk score and recommendations from unstable angina and non-ST elevation myocardial infarction guidelines for patient management based on an associated risk score.

The exemplary pathway method 1320 has the capability of achieving goals of the pathway method 1301 and/or other goals. In particular, the exemplary pathway method 1320 has an ability to create, implement and/or maintain one or more pathways (e.g., an optimal pathway, etc.) in an automated and/or semi-automated manner. For example, as shown in FIG. 13, a reception block 1322 receives information from any of a variety of sources, such as, but not limited to, the aforementioned databases, a patient, a physician, and/or a device. In addition, the reception block 1322 optionally receives information related to implementation of one or more pathways (e.g., an optimal pathway, etc.). An analysis block 1324 follows the reception block 1322 wherein analysis of received information and/or other information occurs. For example, as discussed above, an exemplary server makes one or more models available to a client wherein the client (e.g., automatically and/or through a user) uses the one or more models to create one or more pathways (e.g., an optimal pathway, etc.). A determination block 1326 determines one or more suitable pathways, for example, based on the analysis of the analysis block 1324. According to the exemplary method 1320, the determination may occur in an automated and/or semi-automated manner. After a pathway determination occurs, implementation follows in an implementation block 1328. Implementation optionally occurs in an automated and/or semi-automated manner. For example, where a patient has been prescribed and/or fitted (externally and/or internally) with a device, such as, but not limited to, an ICD, implementation optionally occurs via communication directly and/or indirectly to the device. Further, in an exemplary client-based system, such an exemplary method optionally occurs in conjunction with a client (e.g., the client 860 of FIGS. 8–12) having a communication link to a patient device wherein implementation occurs via this communication link.

Overall, the exemplary method 1320 has an ability to shift typically time consuming tasks, such as, assembling a team and consensus building, to a stage that does not interfere with patient treatment. Such an exemplary method can, for example, optionally reduce costs, minimize physician-patient face-to-face interaction, enhance and/or expedite decision making, and provide a better patient experience (e.g., better outcome, less time consuming for patient, more flexibility in pathway parameters and/or device operation, etc.).

Figure 14:
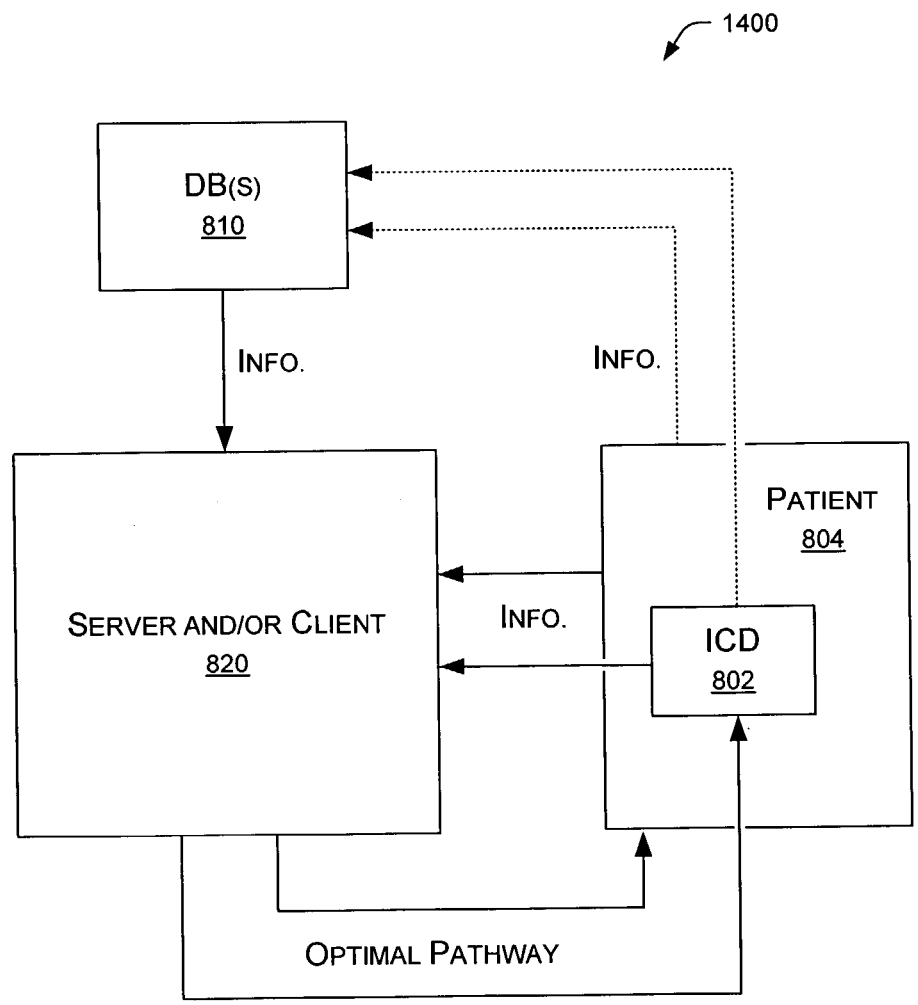
FIG. 14 is a functional block diagram of an exemplary system and/or method for managing one or more patient pathways.

FIG. 14 shows an exemplary system and/or method 1400. This exemplary system and/or method 1400 is optionally suitable for compliance with one or more of the various features and/or functions discussed with reference to the exemplary method 1320 of FIG. 13. The exemplary system and/or method 1400 includes a database block 810, a server and/or client block 820 and a patient block 804 having an associated ICD block 802. The database block 810 includes one or more databases and/or associated computing devices capable of providing information to the server and/or client block and optionally capable of receiving information from the patient block 804 and/or ICD block 802. The server and/or client block 820 typically receives information from the database block 810 while it may also receive information from the patient block 804 and/or the ICD block 802. In addition, the server and/or client block 820 has an ability to communicate with the patient block 804 and/or the ICD block 802 whereby communication aids in pathway management. For example, the server and/or client block 820 optionally receives information from one or more source (e.g., the database block 810, the patient block 804, the ICD block 802, etc.) and analyzes the received information and/or other information (e.g., input from a physician and/or other healthcare industry worker) to determine one or more suitable pathways for the patient 804. Further, the one or more suitable pathways are optionally based, at least in part, on capabilities of the ICD block 802 (e.g., pacemaker, neurostimulation device, drug-delivery device, etc.).

The exemplary system and/or method 1400 optionally operate in a closed-loop manner. For example, an exemplary pathway maintenance scheme monitors and/or adjusts pathway parameters over time responsive to a time-dependent plan and/or other variable that may change with respect to time. Further, such an exemplary pathway maintenance scheme optionally monitors and/or adjusts pathway parameters in an automated and/or semi-automated manner. In this manner of operation, efficiencies may be gained in cost, resource use, and/or patient outcome.

In another example, the exemplary system and/or method 1400 automatically or manually account for availability of a new drug, which may allow for significantly improved treatment. In this example, the new drug may require a different method of use by a patient than a previous drug. The exemplary system and/or method 1400 can account for the new drug (e.g., via information entered in the database(s) block 810) and in response, update CHF pathways and/or pathway models. The exemplary system and/or method 1400 may then apply these updates to all the client software subsystems, thereby applying the new changes to each of the patients, or providing the ability for a physician to use the new drug and thereby provide an improved and different clinical pathway for any particular patient.

In another example, the exemplary system and/or method 1400 accounts for new methods of pacing the left ventricle in bi-ventricular pacing schemes, which may be particularly helpful in the treatment of CHF patients. Such new methods of pacing may be entered into a database and subsequently used to update models and/or pathways. The updated CHF pathways are then communicated to physicians and/or to patients (e.g., via communication links).

As described herein, pathway parameters may include parameters related to operation of an implantable cardiac device (see, e.g., operational parameters in description of an exemplary ICD device above). An operational parameter may also be related to a pathway and, in particular, related to and/or necessary for implementation of a pathway. Where applicable, various operational parameters include, but are not limited to, morphology discrimination parameters, template update parameters, sudden onset parameters, interval stability parameters, time to diagnosis parameters, time to therapy parameters, sensitivity control parameters, fibrillation detection interval parameters, tachycardia detection interval parameters, left ventricular pacing parameters, therapy inhibition parameters, and rate-responsive bradycardia therapy parameters. Hence, an exemplary method for treating CHF may include creating a pathway for treating CHF using one or more analytical models having pathway and/or operational parameters; implementing the pathway, at least in part, by communicating one or more pathway and/or operational parameters to an ICD; and maintaining the pathway, at least in part, by receiving information from the ICD wherein the received information may include pathway and/or operational parameters or other information.

Figure 15:
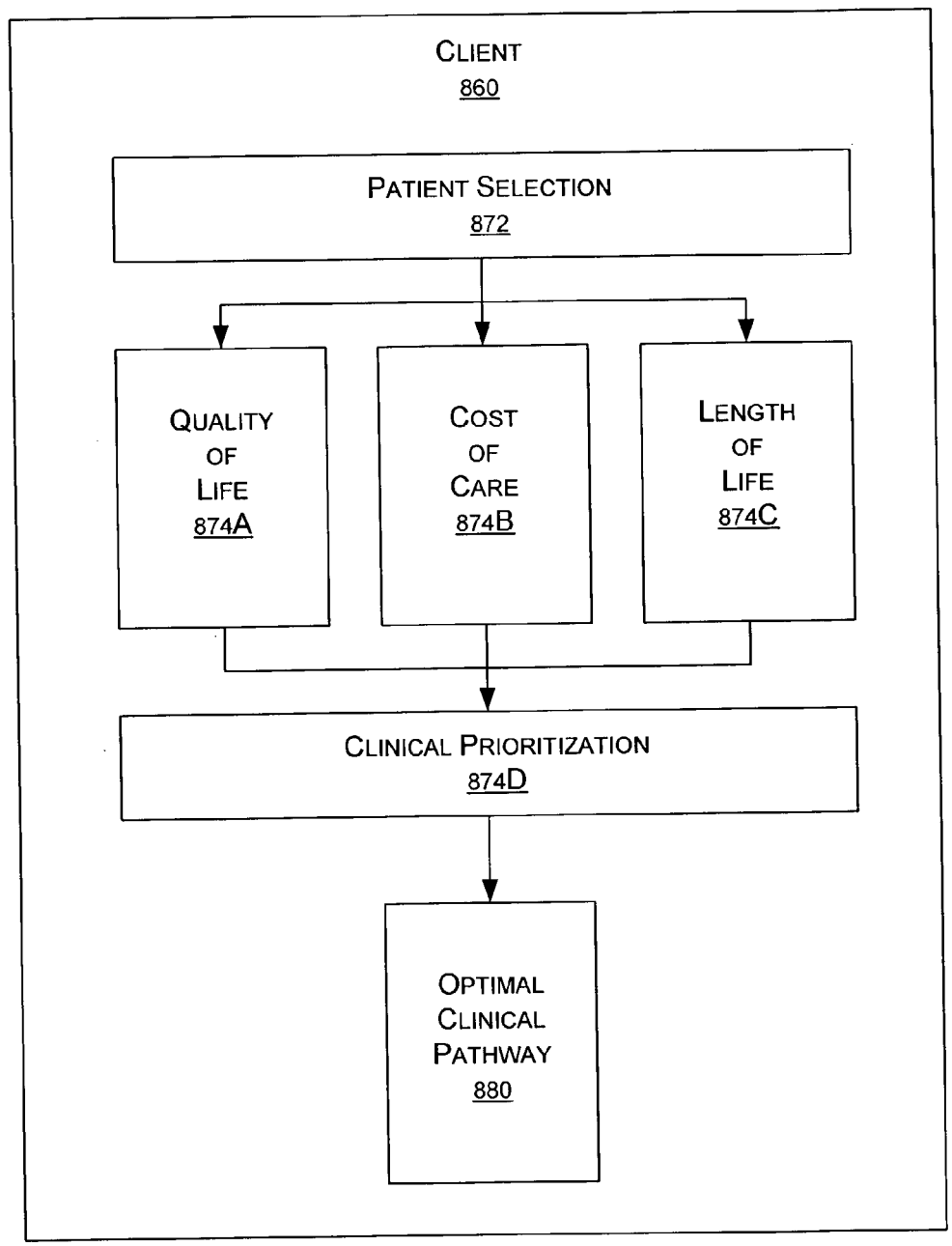
FIG. 15 is a functional block diagram of an exemplary client and/or method for arriving at a pathway.

FIG. 15 shows an exemplary client 860 and an associated exemplary method. In a patient selection block 872 (e.g., see the patient block 872 of FIGS. 9, 12), the client 860 selects a patient. Next, in one or more analysis blocks 874A, 874B, 874C, the client 860 uses one or more models to analyze quality of life in the analysis block 874A, cost of care in the analysis block 874B, and/or length of life in the analysis block 874C. Such analyses optionally produce associated information with respect to time. Further, the client optionally creates a user-interface to display and/or allow user-interaction with the associated information. For example, wherein user intervention occurs, a user optionally views and/or modifies (e.g., overrides model information, etc.) cost of care information (and/or, e.g., quality of life, length of life, etc.) with respect to time. While such intervention optionally occurs within an analysis block 874A, 874B, 874C, it may also occur in a clinical prioritization block 874D. In general, the clinical prioritization block 874D allows for consideration of a patient and/or group criterion or criteria (e.g., demographic, insurance, political, family, device, etc.) in determination of one or more suitable pathways for the patient. For example, the clinical prioritization block 874D optionally uses a patient associated quality of life index, cost of care index and/or length of life index to weight and/or otherwise prioritize aspects of the analyses 874A, 874B, 874C, etc. Note that various exemplary analyses blocks are presented below with reference to FIGS. 16–18.

The clinical prioritization block 874D optionally operates in an automated and/or a semi-automated manner. For example, at the onset of diagnosis and/or original pathway implementation, criteria are communicated to the client 860 and/or otherwise made available to the client 860. In such an exemplary system and/or method, pathway management considers such criteria to monitor and/or adjust one or more pathways. In general, the client 860, in an optimal clinical pathway block 880, arrives at an optimal clinical pathway for the patient selected and/or otherwise input in the patient selection block 872. Again, as discussed with respect to the exemplary system and/or method 1400 of FIG. 14, the client 860 optionally communicates the optimal pathway to a patient (e.g., the patient 804, etc.) and/or a device (e.g., the ICD 804, etc.) associated with the patient.

Figure 16:
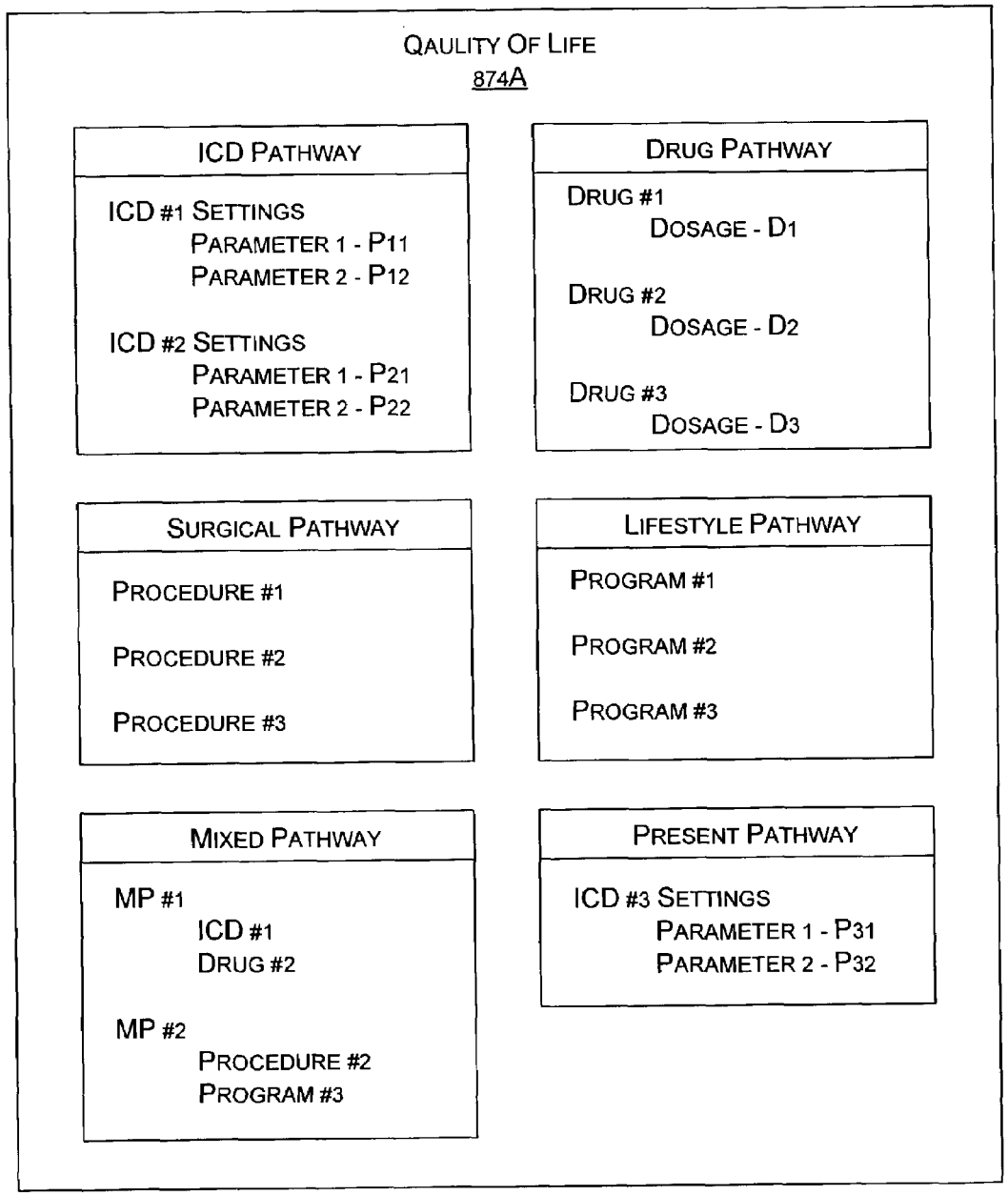
FIG. 16 is a functional block diagram of an exemplary quality of life analysis block for use in pathway management.

FIG. 16 shows the exemplary quality of life block 874A of FIG. 15 along with exemplary detail. The quality of life block 874A optionally analyzes information using a model, such as, but not limited to, a model made available by a server (e.g., the server 840 of FIG. 8, etc.), to create one or more potentially suitable pathways. For example, implantable cardiac device (ICD) pathways include ICD #1 (e.g., parameters P11, P12) and ICD #2 (e.g., parameters P21, P22); drug pathways include Drug #1 (e.g., dosage D1), Drug #2 (e.g., dosage D2), and Drug #3 (e.g., dosage D3); surgical pathways include Procedure #1, Procedure #2, and Procedure #3; lifestyle pathways include Program #1, Program #2, and Program #3; and mixed pathways include MP #1 (e.g., ICD #1, Drug #2) and MP #2 (e.g., Procedure #2, Program #3). The quality of life block 874A optionally includes one or more present pathways as well, for example, ICD #3 (e.g., parameters P31, P32). Thus, according to this exemplary quality of life analysis scenario, the exhibited potential pathways differ from the present pathway. Of course, a patient may not have a present pathway depending on course.

Figure 17:
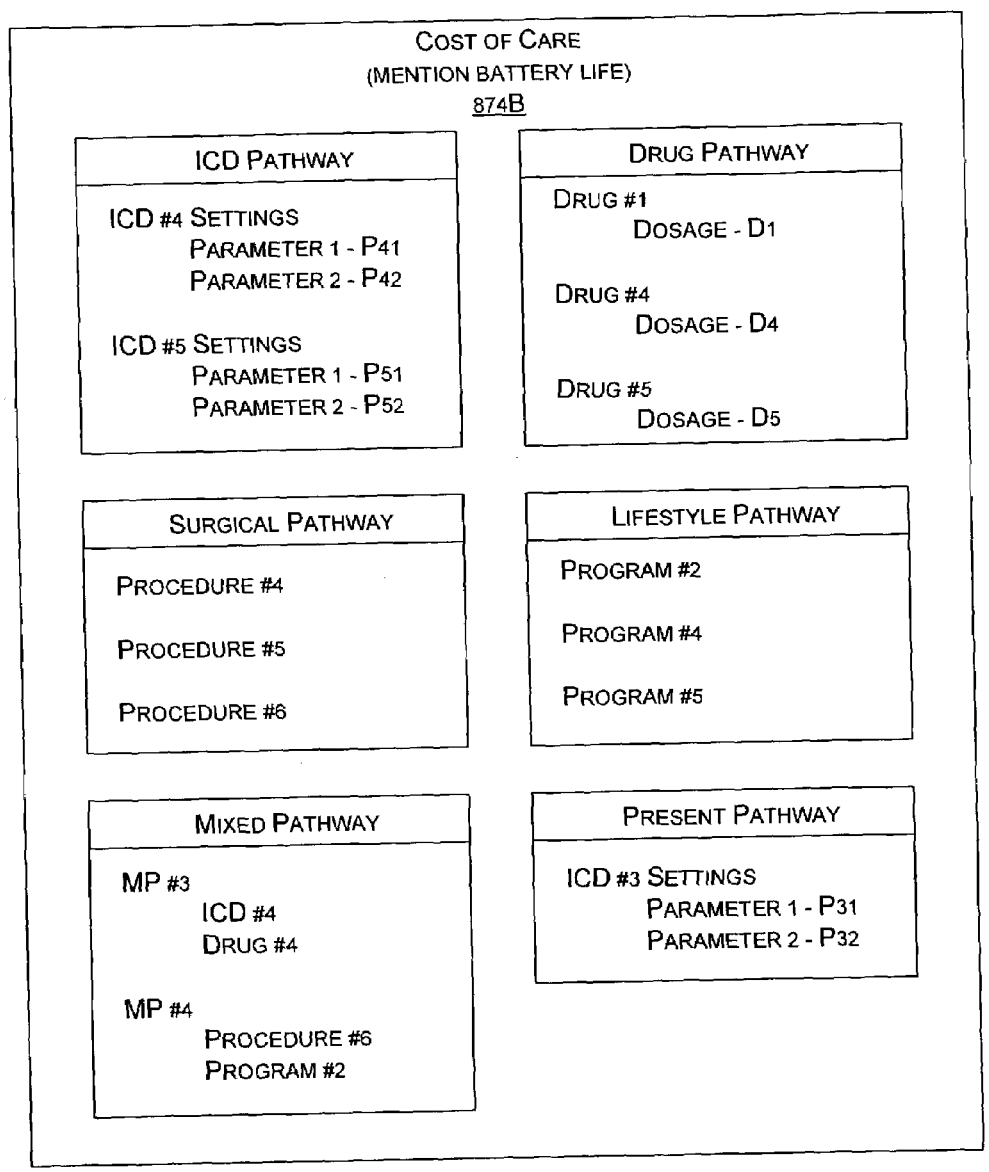
FIG. 17 is a functional block diagram of an exemplary cost of care analysis block for use in pathway management.

FIG. 17 shows the exemplary cost of care block 874B of FIG. 15 along with exemplary detail. The cost of care block 874B optionally analyzes information using a model, such as, but not limited to, a model made available by a server (e.g., the server 840 of FIG. 8, etc.), to create one or more potentially suitable pathways. For example, implantable cardiac device (ICD) pathways include ICD #4 (e.g., parameters P41, P42) and ICD #5 (e.g., parameters P51, P52); drug pathways include Drug #1 (e.g., dosage D1), Drug #4 (e.g., dosage D4), and Drug #5 (e.g., dosage D5); surgical pathways include Procedure #4, Procedure #5, and Procedure #6; lifestyle pathways include Program #2, Program #4, and Program #5; and mixed pathways include MP #3 (e.g., ICD #4, Drug #4) and MP #4 (e.g., Procedure #6, Program #2). The cost of care block 874B optionally includes one or more present pathways as well, for example, ICD #3 (e.g., parameters P31, P32). Thus, according to this exemplary cost of care analysis scenario, the exhibited potential pathways differ from the present pathway. Of course, a patient may not have a present pathway depending on course.

The cost of care analysis may include factors such as time to replacement of an implantable cardiac device, power source (e.g., battery), lead, etc. Often replacement costs are significant and have a direct bearing on quality of life and/or length of life.

Figure 18:
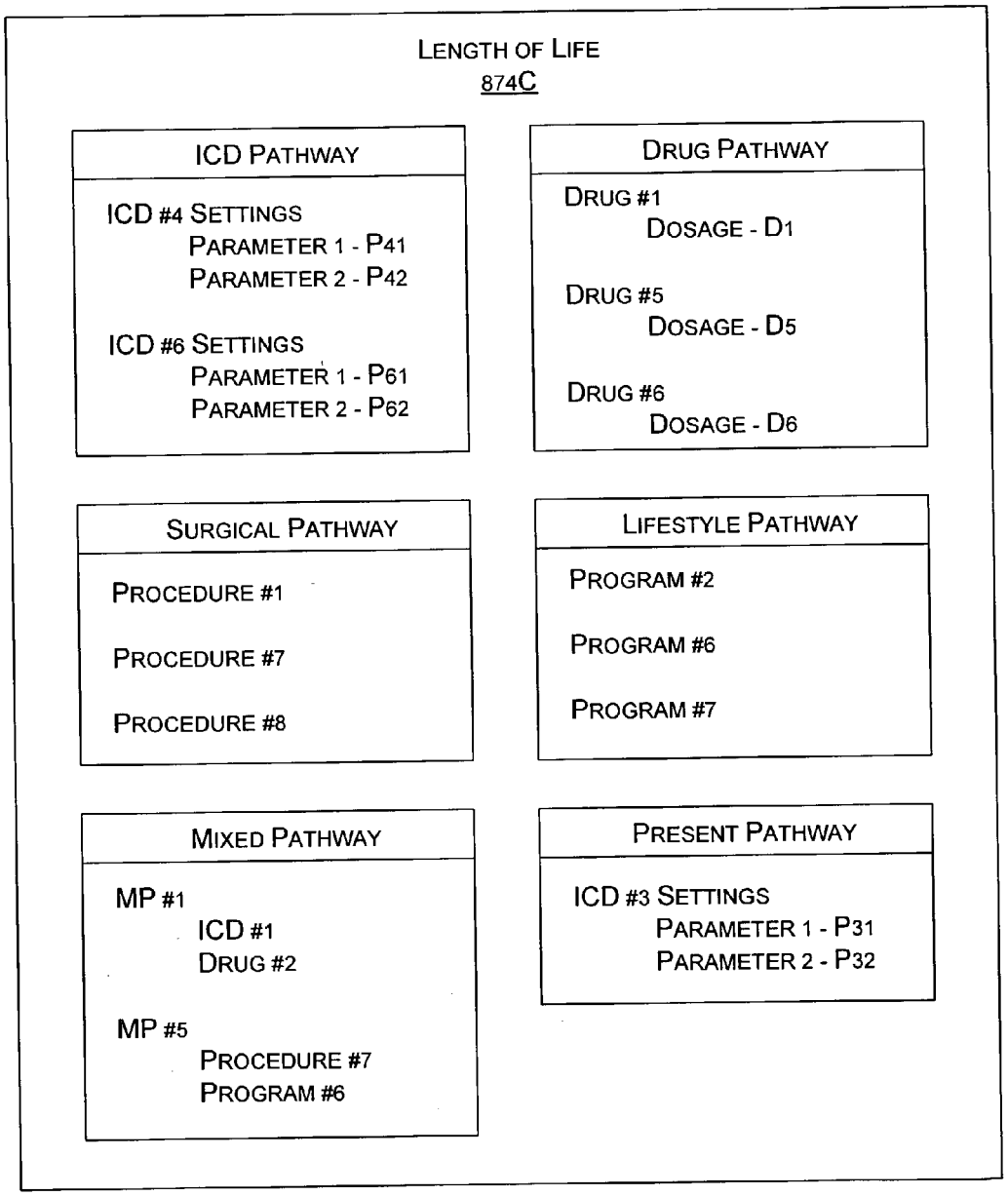
FIG. 18 is a functional block diagram of an exemplary length of life analysis block for use in pathway management.

FIG. 18 shows the exemplary length of life block 874C of FIG. 15 along with exemplary detail. The length of life block 874C optionally analyzes information using a model, such as, but not limited to, a model made available by a server (e.g., the server 840 of FIG. 8, etc.), to create one or more potentially suitable pathways. For example, implantable cardiac device (ICD) pathways include ICD #4 (e.g., parameters P41, P42) and ICD #6 (e.g., parameters P61, P62); drug pathways include Drug #1 (e.g., dosage D1), Drug #5 (e.g., dosage D5), and Drug #6 (e.g., dosage D6); surgical pathways include Procedure #1, Procedure #7, and Procedure #8; lifestyle pathways include Program #2, Program #6, and Program #7; and mixed pathways include MP #1 (e.g., ICD #1, Drug #2) and MP #5 (e.g., Procedure #7, Program #6). The length of life block 874C optionally includes one or more present pathways as well, for example, ICD #3 (e.g., parameters P31, P32). Thus, according to this exemplary length of life analysis scenario, the exhibited potential pathways differ from the present pathway. Of course, a patient may not have a present pathway depending on course.

Figure 19:
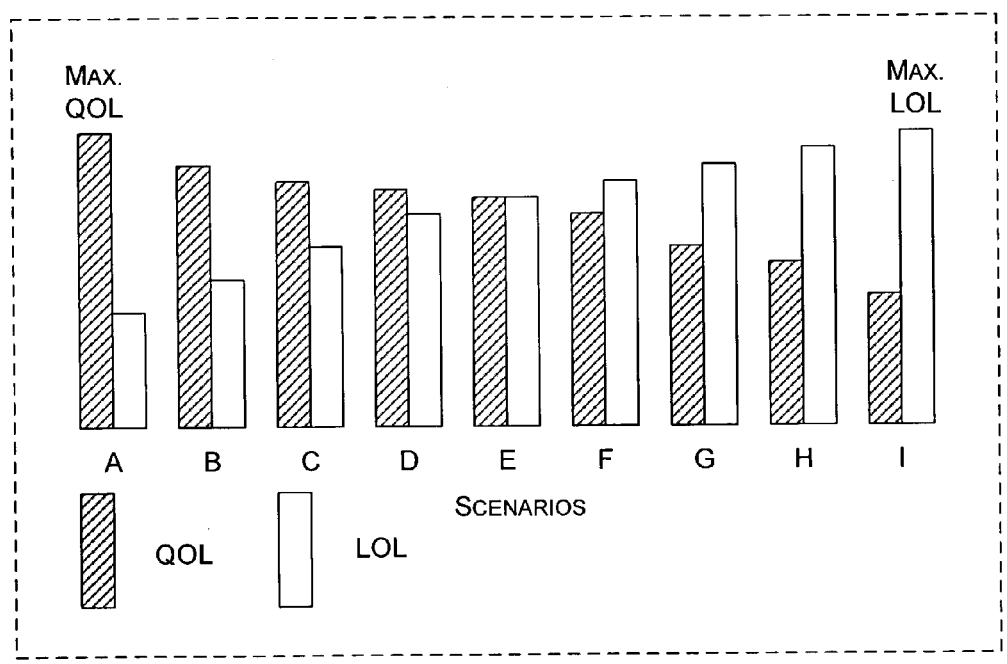
FIG. 19 is a graph of an exemplary analysis that includes information pertaining to quality of life and/or length of life.

FIG. 19 shows an exemplary analysis 1900. The exemplary analysis 1900 includes a bar-graph plot of quality of life and length of life for various scenarios, labeled scenario A through I. For example, the plot shows a maximum quality of life and a minimum length of life in scenario A; whereas, a maximum length of life and a minimum quality of life are shown in scenario I. An exemplary client optionally includes user-interface software for presentation of a graph such as the graph 1900 shown in FIG. 19. In such a client, a user optionally determines a pathway with the aid of such a user-interface. For example, if a user desires a compromise between quality of life and length of life, then one of the scenarios B through H may suffice and determine and/or aid in determination of a pathway.

Figure 20:
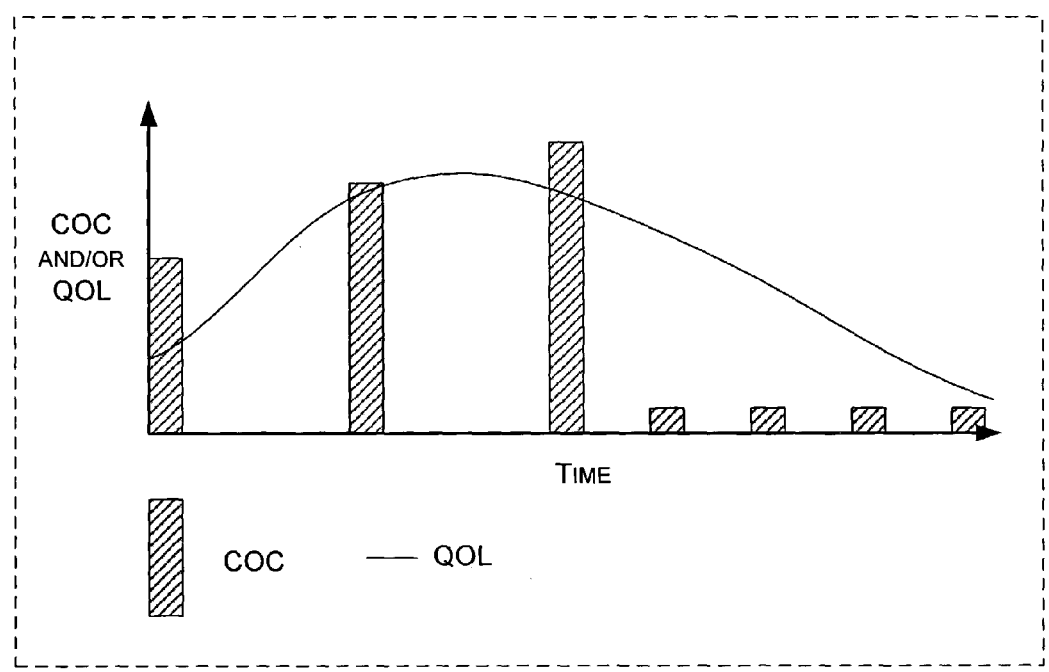
FIG. 20 is a graph of an exemplary analysis that includes information pertaining to quality of life with respect to time and to cost of care with respect to time.

FIG. 20 shows another exemplary analysis 2000. The exemplary analysis 2000 includes a plot of cost of care information and quality of life information with respect to time. The plot of cost of care information with respect to time exhibits seven cost of care allotments. The first three of these allotments have a cost significantly greater than the latter four allotments. In a user-interactive client, a user optionally edits the cost of care information with respect to time. For example, a user may delete one of the first three cost of care allotments which may correspond to foregoing a treatment, such as, but not limited to, a surgery. Upon such a deletion, an analytical block associated with cost of care optionally determines whether the deletion is allowable and/or whether a potential pathway exists for the edited cost of care with respect to time. Further, the edit in cost of care with respect to time may optionally provide information to a quality of life analysis block, which, in turn, optionally determines new quality of life information with respect to time. A user, in a user-interactive client scheme, may also edit the quality of life information with respect to time. Such an edit optionally provides information to a cost of care analysis block, which, in turn, optionally determines new cost of care information with respect to time. Of course, length of life information and/or other information is optionally presentable by an exemplary client in such an exemplary analysis.

While the exemplary analysis 2000 of FIG. 20 optionally allows for user-interaction to aid in determination of a pathway (e.g., pathway creation, implementation and/or maintenance), such an exemplary analysis is optionally presented and/or otherwise made available to a user, patient, etc.

Figure 21:
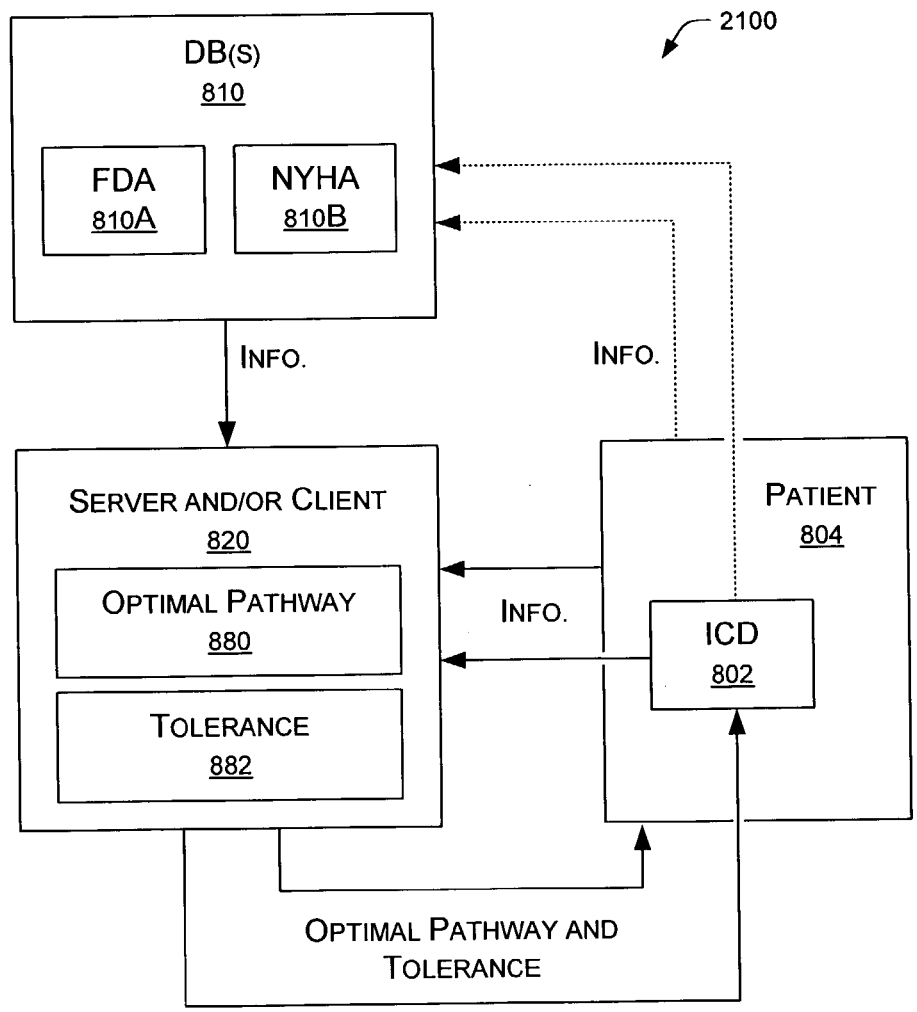
FIG. 21 is a functional block diagram of an exemplary system and/or method for managing a patient pathway using one or more tolerances.

FIG. 21 shows an exemplary system and/or method 2100 that includes various components and/or functional features of the exemplary system and/or method 1400 of FIG. 14. As shown in FIG. 21, a database block 810 includes, for example, a food and drug administration (FDA) information database 810A and a New York Heart Association (NYHA) information database 810B, and further includes a communication link with a server and/or client block 820 and/or a patient block 804 and/or an implantable cardiac device (ICD) block 802 associated with the patient block 804. The server and/or client block 820 includes an optimal pathway block 880 and a tolerance block 882.

According to the exemplary system and/or method 2100, the server and/or client block 820 has a communication link for communicating information to the patient block 804 and/or the ICD block 802 associated with the patient block 804. The exemplary system and/or method 2100 also includes one or more communication links for communicating information between the patient block 804 and/or ICD block and the server and/or client block 820.

The optimal pathway block 880 optionally operates in a manner described above with reference to the client 860 of FIG. 15. The tolerance block 882 optionally allows for use of one or more tolerances for information germane to a pathway, for example, an optimal pathway of the optimal pathway block 880. Tolerances, as discussed herein, can allow for enhanced automation of pathway management. For example, many ICDs are capable of automatic operation for extending periods of time without intervention. To operate automatically for extending periods of time, many ICDs incorporate safety measures that ensure that the ICD will not operate in a manner detrimental and/or intolerable to a patient. Such operation and/or safety measures typically require approval from a body such as the U.S. Food and Drug Administration (FDA). While an exemplary ICD optionally includes such safety measures, use of one or more tolerances optionally allows for automatic operation in a system loop that extends beyond the ICD. In turn, duration of automatic operation can be lengthened to any particularly allowable degree wherein breach of one or more tolerance optionally leads to intervention.

Figure 22:
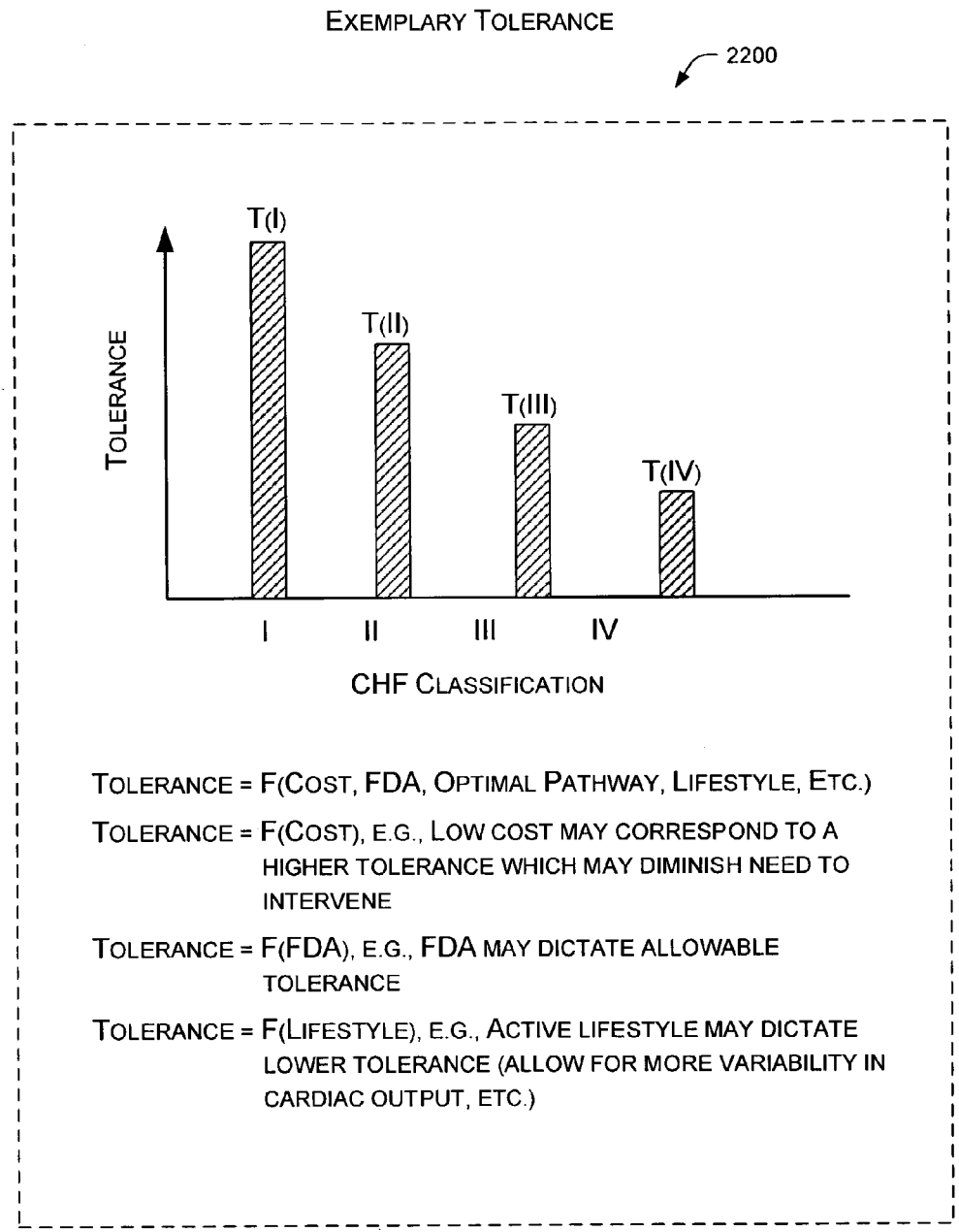
FIG. 22 is graph of an exemplary tolerance as a function of CHF classification (e.g., NYHA classifications).

FIG. 22 shows an exemplary tolerance graph 2200. According to this exemplary scenario 2200, tolerance depends, at least in part, on, for example, NYHA classifications wherein tolerance decreases with respect to an increase in NYHA classification. Of course, tolerance may depend on any of a variety of factors, such as, but not limited to, cost, pathway, lifestyle, etc.). For example, a tolerance based at least in part on cost may result in a higher tolerance when a lower cost of care is desirable (e.g., to diminish a need to intervene, etc.); whereas, a tolerance based at least in part on lifestyle may result in a higher tolerance when a patient has an active lifestyle wherein variability in cardiac function may be expected.

Figure 23:
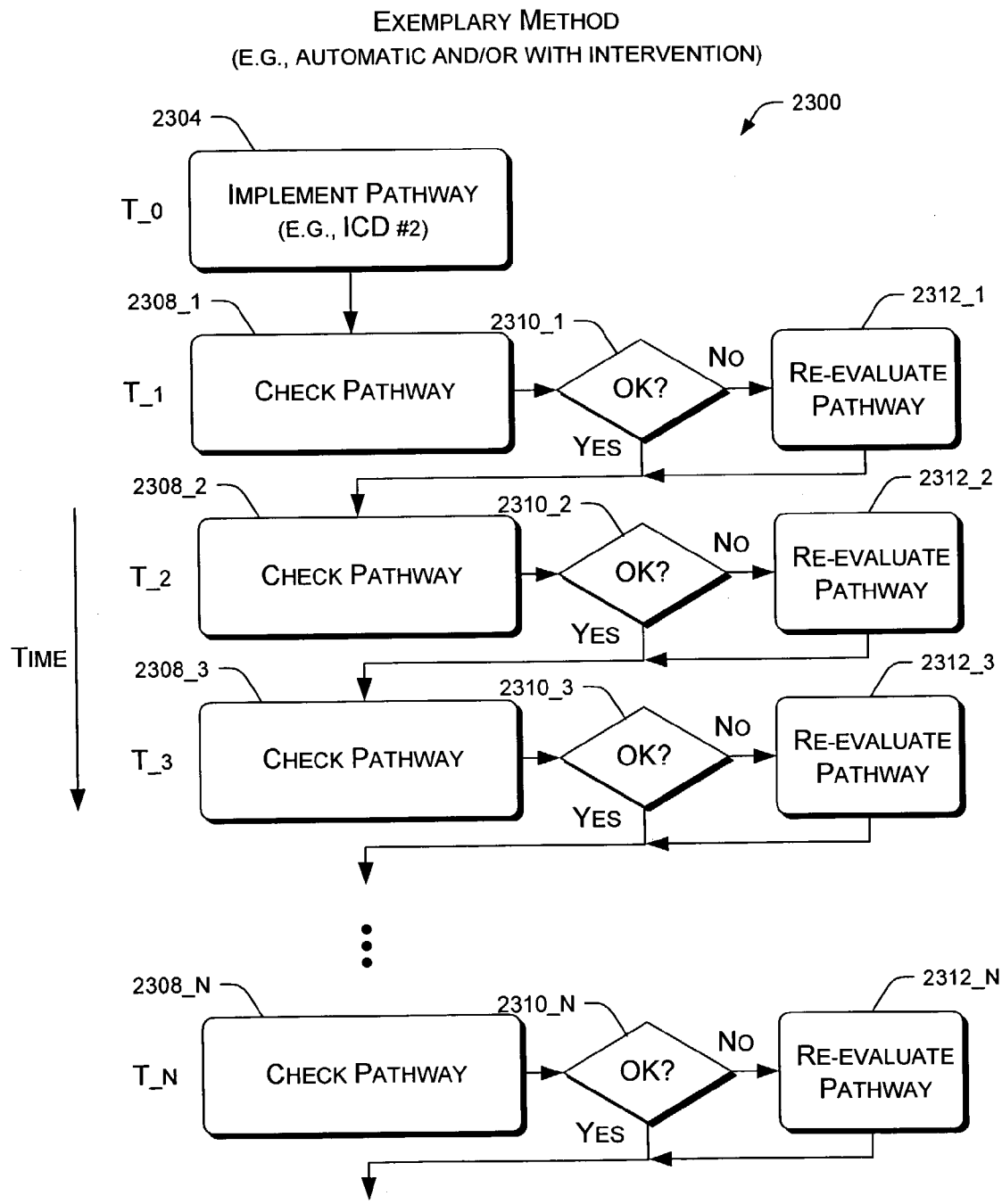
FIG. 23 is a functional block diagram of an exemplary method for managing a patient pathway.

FIG. 23 shows an exemplary periodic method 2300. In an implementation block 2304, a client implements a pathway at a time $T\_0$. At a latter time $T\_1$, a check block 2308_1 checks the pathway, for example, initiates retrieval and/or input of information germane to the implemented pathway. A decision block 2310_1 follows that determines, for example, whether the pathway meets one or more criteria (e.g., tolerance and/or other criteria). If the decision block 2310_1 determines that the pathway does not meet the one or more criteria, then a re-evaluation block 2312_1 follows wherein implementation of a new and/or modified pathway optionally occurs. If the decision block 2310_1 determines that the pathway meets the one or more criteria, then operation continues. Subsequent check pathway blocks 2308_2, 2308_3, 2308_N follow according to a set period and/or on a time basis determined by, for example, a prior check block and/or evaluation block. Thus, an exemplary method for managing a CHF pathway optionally includes checks, which, in turn, are optionally part of an overall CHF pathway.

Figure 24:
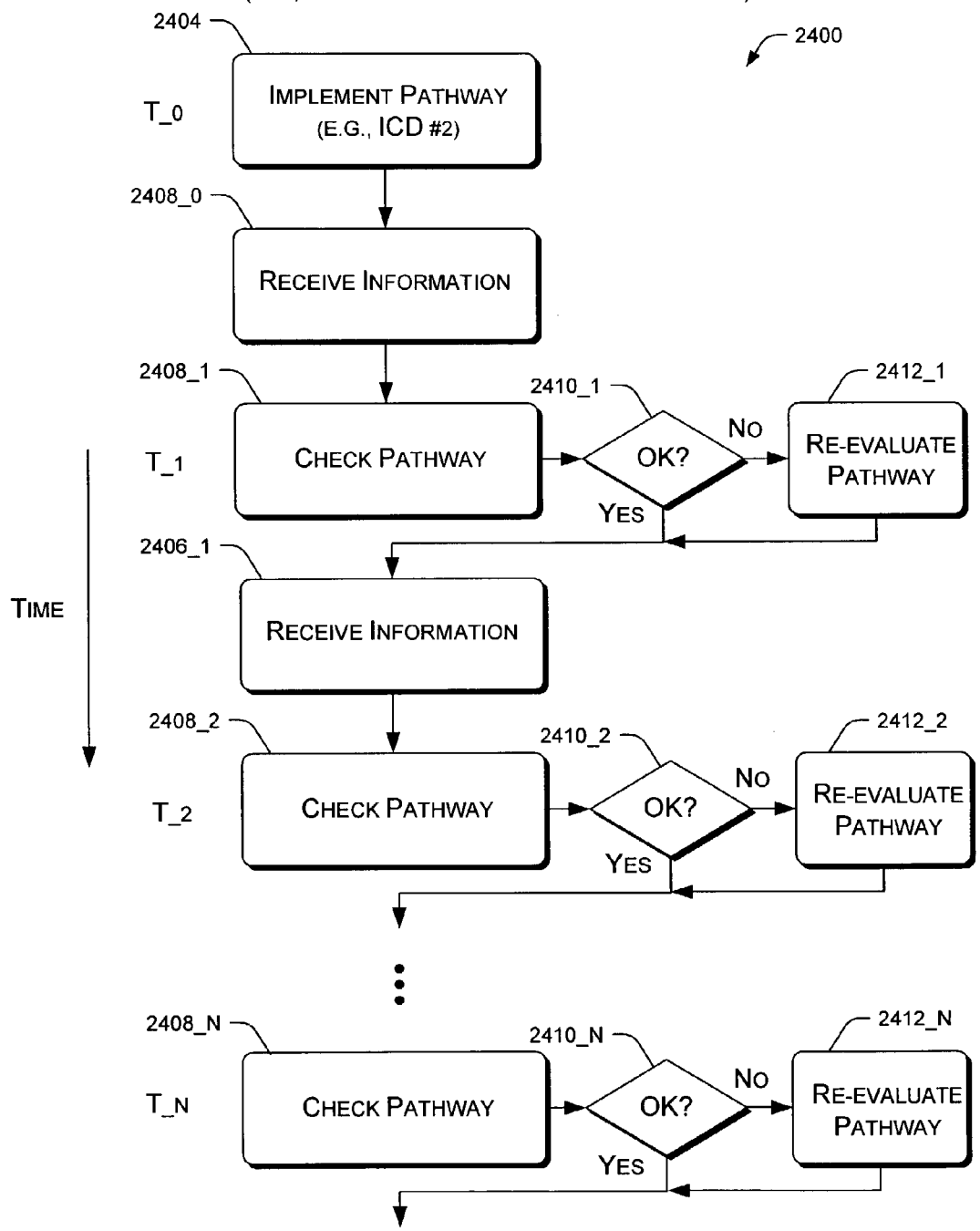
FIG. 24 is a functional block diagram of an exemplary method for managing a patient pathway.

FIG. 24 shows an exemplary periodic method 2400 that includes information reception at and/or between periodic pathway checks. In an implementation block 2304, a client implements a pathway at a time $T\_0$. A reception block 2406_0 follows wherein reception of information germane to a patient pathway occurs. For example, a client, a server, and/or a database receive information from a patient, an ICD, a physician, and/or another source. At a latter time $T\_1$, a check block 2408_1 checks the pathway, for example, initiates retrieval and/or input of information germane to the implemented pathway (e.g., optionally received via a reception block such as the reception block 2406_0). A decision block 2410_1 follows that determines, for example, whether the pathway meets one or more criteria (e.g., tolerance and/or other criteria). If the decision block 2410_1 determines that the pathway does not meet the one or more criteria, then a re-evaluation block 2412_1 follows wherein implementation of a new and/or modified pathway optionally occurs. If the decision block 2410_1 determines that the pathway meets the one or more criteria, then operation continues, for example, at a reception block 2406_1. Thereafter, subsequent check pathway blocks 2408_2, 2408_N follow according to a set period and/or on a time basis determined by, for example, a prior check block, evaluation block and/or a reception block. Thus, an exemplary method for managing a CHF pathway optionally includes information reception and/or checks, which, in turn, are optionally part of an overall CHF pathway.

Figure 25:
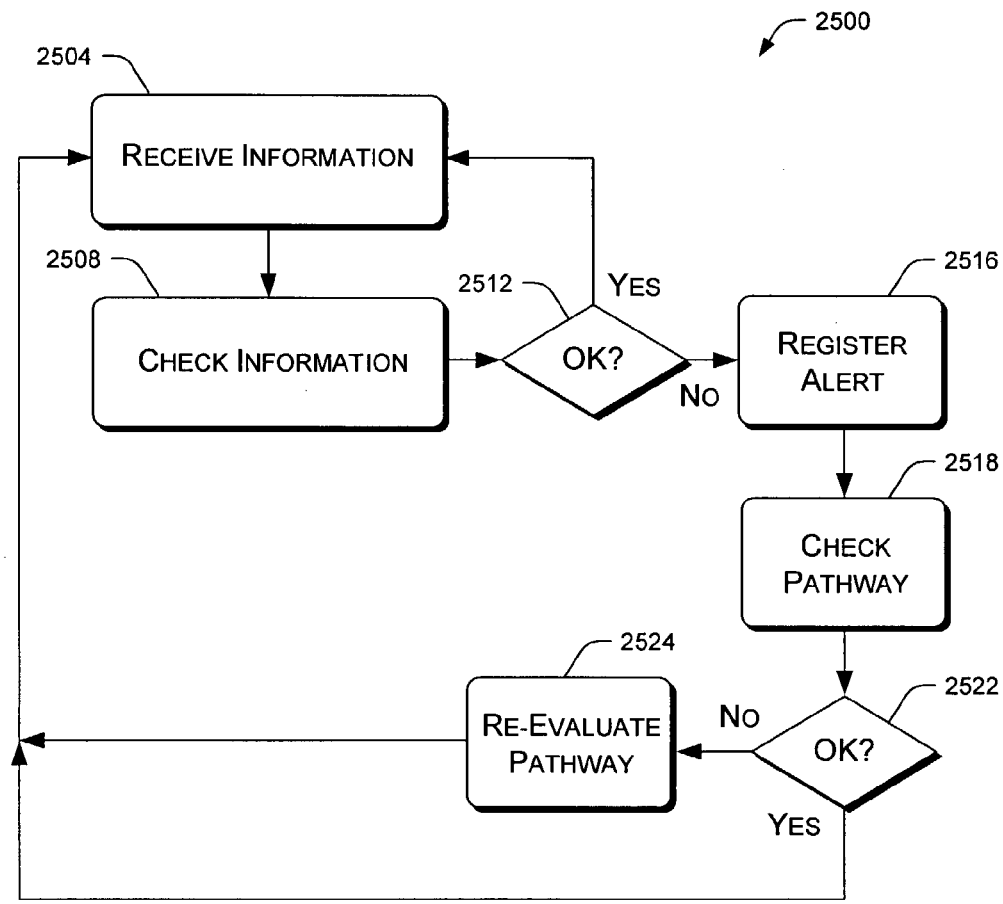
FIG. 25 is a functional block diagram of an exemplary method having an optional alert.

FIG. 25 shows an exemplary method 2500 for checking information and optionally issuing and/or registering alerts. In a reception block 2504, a client, a server and/or a database receives information germane to a patient pathway. A check information block 2508 follows that checks the information using one or more criteria. Next, a decision block 2512 determines, for example, whether the received information meets one or more criteria (e.g., tolerance and/or other criteria). If the decision block 2512 determines that the received and/or other information meets the one or more criteria, then operation continues, for example, at the reception block 2504. If the decision block 2512 determines that the received and/or other information does not meet one or more criteria, then a registration block 2516 follows that registers the failure and/or issues an alert (e.g., an alert for intervention and/or an alert to schedule a fix and/or modification). The exemplary method 2500 then continues at another check block 2518. The check block 2518 checks the pathway, for example, initiates retrieval and/or input of information germane to the implemented pathway (e.g., optionally received via a reception block such as the reception block 2504). Another decision block 2522 follows that determines, for example, whether the pathway meets one or more criteria (e.g., tolerance and/or other criteria). If the decision block 2522 determines that the pathway does not meet the one or more criteria, then a re-evaluation block 2524 follows wherein implementation of a new and/or modified pathway optionally occurs. Thereafter, the exemplary method 2500 optionally continues at the reception block 2504. If the decision block 2522 determines that the pathway meets the one or more criteria, then operation continues, for example, at a reception block 2504.

Figure 26:
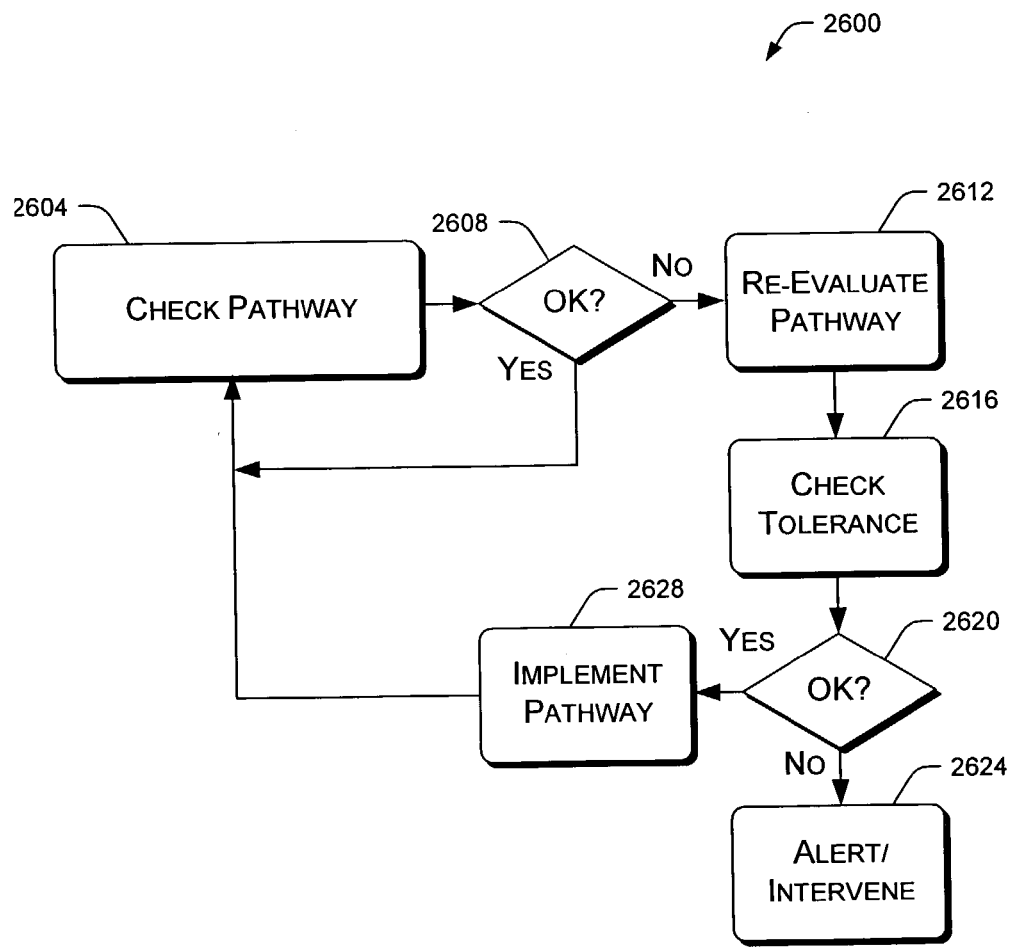
FIG. 26 is a functional block diagram of an exemplary method for managing a patient pathway using one or more tolerances.

FIG. 26 shows an exemplary method 2600 for managing a patient pathway. According to the exemplary method 2600, a check block 2604 checks a patient pathway, for example, initiates retrieval and/or input of information germane to the implemented pathway. A decision block 2608 follows that determines, for example, whether the pathway meets one or more criteria (e.g., tolerance and/or other criteria). If the decision block 2608 determines that the pathway meets the one or more criteria, then operation continues, for example, at the check block 2604. If the decision block 2608 determines that the pathway does not meet the one or more criteria, then a re-evaluation block 2612 follows wherein implementation of a new and/or modified pathway optionally occurs. Thereafter, another check block 2616 checks one or more tolerances as applied to the new and/or modified pathway. Another decision block 2620 follows that determines, for example, whether the new and/or modified pathways meets the one or more tolerances (e.g., optionally including FDA and/or other guidelines). In this example, tolerances (which may also be modified) are checked or monitored in response to pathway modification (e.g., creation of a new and/or modified pathway). If a new and/or modified pathway passes such a tolerance check, then in an implementation block 2628, pathway implementation occurs. However, if the tolerance check fails, then an alert and/or intervention block 2624 follows that issues and/or registers an alert, possibly calling for intervention.

Overall, trust is optionally designed into an exemplary system and/or method through use of one or more tolerances. In general, ICDs may use internal tolerances to operate in an automated manner; various exemplary systems and/or methods presented herein optionally use external tolerances to allow for at least periods of automated operation that includes a wealth of information and/or models that are generally not available on an internal device basis.

Figure 27:
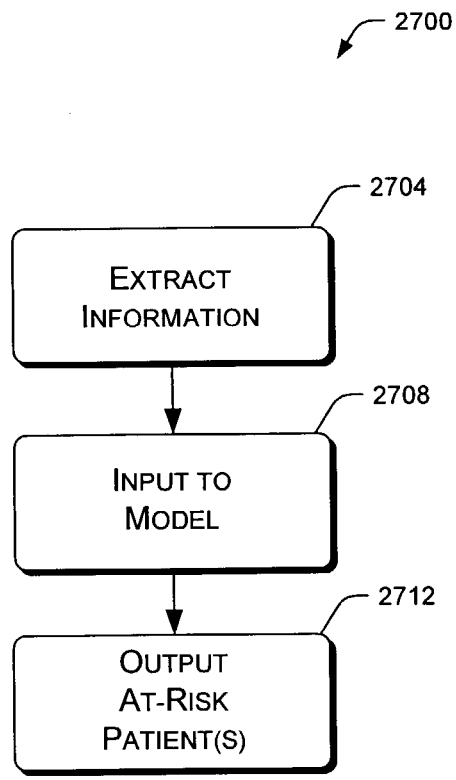
FIG. 27 is a functional block diagram of an exemplary method for identifying at-risk patients.

FIG. 27 shows an exemplary method 2700 for identifying one or more at-risk CHF patients. In an extraction block 2704, extraction of information occurs for a selected patient. An input block 2708 inputs the extracted information and/or other information into a CHF model. The CHF model may assign a risk value to each of the patients. Next, an output block 2712 outputs information, based at least in part on the CHF model, that identifies one or more at-risk patients. For example, the at-risk patients may be identified as those having a risk value above a pre-determined level. Such a system may also extract information for patients with confirmed CHF to determine a subset with likely adverse health outcomes. Depending on circumstances, the patient population subset may be targeted for more aggressive treatment. In addition, the exemplary method 2700 may include monitoring of a healthcare provider's medical records on a periodic basis to maintain a vigilant watch of patients and their progress. For example, an exemplary system may scan a physician's records daily, in the early morning hours, and provide treatment pathway adjustments (electronically or in paper form) for automatic implementation and/or care provider implementation (e.g., after review and approval at the beginning of a morning shift). Adjustments may include scheduling additional office, clinic, or hospital patient appointments, services, or training at appropriate times; taking action to (re)order, schedule, or deliver diagnostic tests, drugs, medical equipment, or supplies as required by a treatment plan; periodic scheduling and automatic electronic or physical plan and status report generating for a patient; means for alerting a physician as to important changes in a patient's disease state that may require automated (e.g., machine-centric) or manual (e.g., physician-centric) response or intervention in a timely manner. Of course, various features may enhance a physician's ability to perform at or above national practice standards and regulations and/or permit a physician to incorporate his or her requirements and preferences for treating patients with CHF.

Figure 28:
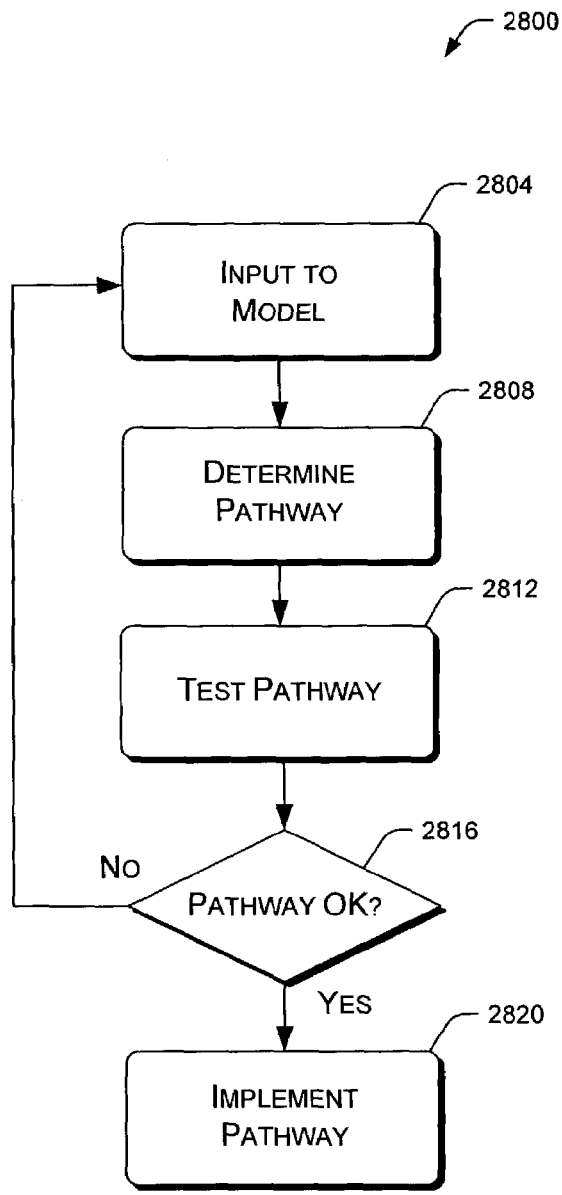
FIG. 28 is a functional block diagram of an exemplary method for testing pathways.

FIG. 28 shows an exemplary method 2800 for testing a CHF pathway. An input block 2804 inputs information to a CHF model capable of determining CHF pathways and/or information relevant to CHF pathways. For example, the input block may input information regarding a patient into a CHF pathway development model. Next, in a determination block 2808, the CHF model determines a CHF pathway. A test block 2812 follows wherein the CHF pathway is tested. In the test block 2812, pathway testing may use a patient model and/or an actual patient. For example, the pathway may be input to a patient model that predicts likelihood of one or more patient outcomes. Alternatively, or in addition to, the pathway may be tested on an actual patient. In instances where a pathway is tested on an actual patient, short-term tests may provide information to predict long-term prognosis of pathway implementation. A check block 2816 follows wherein the test results are analyzed to determine whether the pathway is suitable. If the pathway is not suitable, the method 2800 continues at the input block 2804, wherein the test results may be used to determine a new pathway. If the CHF pathway is suitable, then implementation occurs in an implementation block 2820 (e.g., automatic and/or manual implementation of the CHF pathway for the patient).

Figure 29:
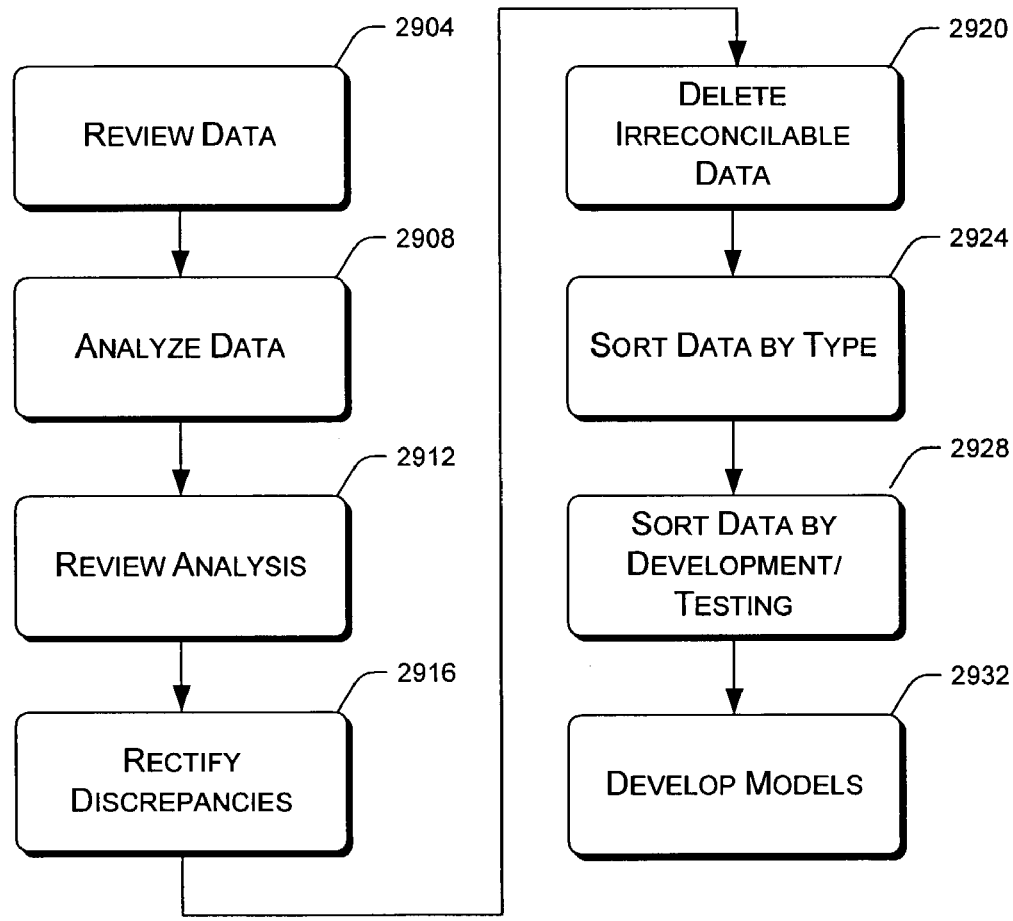
FIG. 29 is a functional block diagram of an exemplary method for processing data prior to model development.

FIG. 29 shows an exemplary method 2900 for processing patient information prior to model development. In a review block 2904, data from various sources is reviewed to determine whether the data are relevant to the purpose of a model. An analysis block 2908 follows wherein a statistical analysis is performed on the relevant data. In another review block 2912, results of the statistical analysis are used to uncover discrepancies in any of the relevant data. Discrepancies may include outliers, improper aggregation, outdated data, etc. A rectification block 2916 aims to rectify discrepancies. For example, questionable data may be presented to a panel of physician reviewers for verification or rectification. A deletion block 2920 acts to delete or remove any irreconcilable data while acceptable data form a pool suitable for model development. The acceptable pool of data may be sorted by data type, such as, claims data, drug data, and diagnostic tests data, etc., in a sort block 2924 to produce data subsets. In turn, subsets are optionally further sorted, in sort block 2928, into development and test subsets suitable for purposes of model construction. For example, some data may be suitable for developing a model while other data may be suitable for testing the model or some data may be reserved for developing a model while other data may be reserved for testing the model. The latter instance ensures that the model can be tested with relevant data that was not used to develop the model.

Yet another exemplary method uses data, such as data processed by the method 2900, for creation of a pathway development model. Such a method analyzes significance levels for selected variables using ANOVA or other appropriate techniques. If a variable has a sufficient significance level for inclusion, it is incorporated into the model. Various techniques may also be used to determine outliers (residual analysis, Cook's distance analysis) by measuring the relative departure of individual patient predictions from actual data-based outcomes. Optimal variable combinations are then determined by pooling variables with common patient population and treatment plan characteristics and performing further regression analyses. In this manner, variable combinations with sufficient significance levels are chosen for incorporation into the model. The model is then tested using test data (see, e.g., the exemplary method 2900).

Various exemplary devices, methods and/or systems disclosed herein help in the management of treatment pathways for CHF patients. Such devices, methods and/or systems optionally rely on accessible medical diagnostic databases, medical therapy databases, medical claims databases, physician-patient specific information and/or other information to develop and manage a long-term (e.g., a lifelong) treatment plan for an individual patient or a group of patients. While aforementioned devices, methods and/or systems may refer to implantable cardiac devices, other implantable medical devices may also be suitable for use where such devices aid in the diagnosis and/or treatment of CHF. Indeed, a patient may have more than one implanted device that operates to treat CHF. Where a patient has more than one implanted device, communication links between the devices and/or external devices may exist.

As described above, various exemplary methods operate periodically and/or continuously to develop, redevelop and/or manage a pathway. Such methods optionally use an implanted device for diagnostic testing and data acquisition to determine a present disease state and use the same or another implanted device for therapeutic applications of a developed treatment plan as derived from, for example, disease management plans, protocols and models, a recorded history of the patient's disease state transitions, and/or the present state of the patient's disease. Disease management plans, protocols, and models can be previously developed and available for use, or can be derived or augmented on an on-going basis using a patient's previously and/or presently determined disease states. Disease management plans, protocols, and models are optionally derived using data retrieved from a network (e.g., Internet, LAN, etc.), accessible medical diagnostic databases, medical therapy databases, and/or medical claims databases.

CONCLUSION

Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

What is claimed is:

1. A method for treating CHF comprising:
    creating a pathway for treating CHF using one or more analytical models;
    implementing the pathway, at least in part, by communicating one or more parameters to an implantable cardiac device; and
    maintaining the pathway, at least in part, by evaluating information received from the implantable cardiac device, wherein the creating includes prioritizing one or more factors related to quality of life, cost of care, or length of life.

2. The method of claim 1, wherein the creating includes receiving information from one or more databases.

3. The method of claim 1, wherein the creating includes use of at least one of quality of life, cost of care or length of life information.

4. The method of claim 1, wherein the one or more analytical models uses at least one of quality of life with respect to time, cost of care with respect to time or length of life with respect to time.

5. The method of claim 1, wherein the prioritizing includes prioritizing the one or more factors with respect to time.

6. The method of claim 1, wherein the one or more parameters comprise a parameter selected from the group consisting of a fibrillation detection interval parameter, a tachycardia detection interval parameter, a left ventricular pacing parameter, a therapy inhibition parameter, and a rate-responsive bradycardia therapy parameter.

7. The method of claim 1, wherein the one or more parameters includes a tolerance.

8. The method of claim 7, wherein the tolerance determines, at least in part, whether to intervene in the maintaining.

9. The method of claim 1, wherein the maintaining occurs automatically following the implementing.

10. The method of claim 1, wherein the maintaining includes changing or modifying the pathway.

11. The method of claim 10, wherein the changing or modifying depends, at least in part, on the receiving.

12. The method of claim 1, further comprising receiving patient-related information via a Web browser.

13. A method for treating CHF comprising:
    creating a pathway for treating CHF using one or more analytical models that predict a likelihood of one or more patient outcomes for the CHF pathway;
    implementing the pathway, at least in part, by communicating one or more parameters to an implantable cardiac device; and maintaining the pathway, at least in part, by periodically evaluating information received from the implantable cardiac device to determine if the pathway as implemented by the implantable cardiac device satisfies one or more performance criteria and adjusting the pathway if the one or more cardiac performance criteria are not satisfied, wherein the creating includes prioritizing one or more factors related to quality of life, cost of care, or length of life.

14. The method of claim 13, further comprising receiving information from the implantable cardiac device.

15. The method of claim 14, wherein the periodic checking uses the received information.

16. A method for implementing a CHF treatment pathway, comprising:
   inputting information regarding a patient into a CHF treatment pathway development model;
   determining a CHF pathway using the CHF treatment pathway development model;
   testing the CHF pathway using a patient model; and
   responsive to the testing, implementing the CHF treatment pathway on the patient, wherein the determining of a CHF pathway includes prioritizing one or more factors related to quality of life, cost of care, or length of life.

* * * * *